(12) United States Patent
Kamiyanagi et al.

(10) Patent No.: US 7,880,141 B2
(45) Date of Patent: Feb. 1, 2011

(54) RESIN FILM EVALUATION METHOD AND METHOD FOR MANUFACTURING A SEMICONDUCTOR DEVICE

(75) Inventors: Hisako Kamiyanagi, Toyama (JP); Satoshi Sibata, Toyama (JP); Reiki Kaneki, Toyama (JP); Kohei Miyagawa, Toyama (JP)

(73) Assignee: Panasonic Corporation, Osaka (JP)

( * ) Notice: Subject to any disclaimer, the term of this patent is extended or adjusted under 35 U.S.C. 154(b) by 680 days.

(21) Appl. No.: 11/987,185

(22) Filed: Nov. 28, 2007

(65) Prior Publication Data

US 2008/0128616 A1   Jun. 5, 2008

(30) Foreign Application Priority Data

Dec. 1, 2006   (JP) .............................. 2006-325351

(51) Int. Cl.
*G01N 23/00*   (2006.01)
*H01L 21/66*   (2006.01)

(52) U.S. Cl. .................. 250/307; 438/14; 257/E21.521

(58) Field of Classification Search ................. 250/307, 250/306; 438/14; 257/E21.521
See application file for complete search history.

(56) References Cited

U.S. PATENT DOCUMENTS

| | | | | |
|---|---|---|---|---|
| 4,601,095 A | * | 7/1986 | Kikuchi et al. | 438/180 |
| 5,179,034 A | * | 1/1993 | Mori et al. | 438/273 |
| 5,233,459 A | * | 8/1993 | Bozler et al. | 359/230 |
| 5,262,661 A | * | 11/1993 | Kuroda et al. | 257/227 |
| 5,275,695 A | * | 1/1994 | Chang et al. | 216/27 |
| 5,285,094 A | * | 2/1994 | Mori et al. | 257/341 |
| 5,286,987 A | * | 2/1994 | Watanabe | 257/221 |
| 5,293,060 A | * | 3/1994 | Komori et al. | 257/544 |
| 5,324,669 A | * | 6/1994 | Kuroda et al. | 438/75 |
| 5,469,015 A | * | 11/1995 | Kaneko et al. | 313/309 |
| 5,863,834 A | * | 1/1999 | Kawaguchi et al. | 438/625 |

FOREIGN PATENT DOCUMENTS

| | | |
|---|---|---|
| JP | 6-252042 | 9/1994 |
| JP | 2004-191833 | 7/2004 |

\* cited by examiner

*Primary Examiner*—Nikita Wells
*Assistant Examiner*—Johnnie L Smith
(74) *Attorney, Agent, or Firm*—McDermott Will & Emery LLP

(57) ABSTRACT

In the resin film evaluation method and method for manufacturing a semiconductor device applying the resin film evaluation method of the present invention, first, a substrate having a resin film formed on an insulating film with an opening in which the surface of the insulating film is exposed is irradiated with charged energetic particles. Then, the surface potentials of the substrate surface irradiated with charged energetic particles are measured. Based on the measurements, the difference in surface potential between the resin film and the insulating film exposed in the opening is obtained. Based on the difference in surface potential, a physical quantity such as the resin film residue count obtained after a given treatment is predicted. In this way, the degenerated layer formed on the surface of a resin film due to charged energetic particles such as implantation ions can be evaluated in a simple and highly accurate manner.

25 Claims, 13 Drawing Sheets

RESIN FILM EVALUATION METHOD AND METHOD FOR MANUFACTURING A SEMICONDUCTOR DEVICE

CROSS-REFERENCE TO RELATED APPLICATION

The present application claims the benefit of Japanese Patent Application No. 2006-325351 filed Dec. 1, 2006, the subject matter of which is incorporated herein by reference.

BACKGROUND OF THE INVENTION

1. Field of the Invention

The present invention relates to a resin film evaluation method which allows for efficient evaluation of the degree of degeneration of a treated resin film and its removal properties after treating a semiconductor substrate with charged energetic particles using as a mask a resin film including a photosensitive resin film such as a photoresist film, for example, in the manufacturing process of a semiconductor integrated circuit device. And the present invention relates to method for manufacturing a semiconductor device applying the resin film evaluation method.

2. Description of the Related Art

In the manufacturing process of a semiconductor device such as a semiconductor integrated circuit device, it is a common technique to form a pattern of photosensitive resin film such as a photoresist film on a semiconductor substrate and use the pattern as a mask. For example, the pattern is used as a mask to implant impurities such as phosphorus, boron, or arsenic in the semiconductor substrate in ion implantation. Then, for example, the source/drain region and drain extension region of a MOS (metal oxide semiconductor) transistor are formed. In dry etching, the underlying film or semiconductor substrate is exposed to etching gas plasma as the pattern is used as a mask. Then, the underlying film or semiconductor substrate is processed to have a form according to the pattern.

The photoresist film used as a mask in such ion implantation or dry etching is subject to ion bombardment from ions in the ion implantation or plasma in the dry etching. Meanwhile, the surface of the photoresist film is hardened or degenerated. The more ion bombardment the photoresist is subject to, the more the surface is hardened or degenerated (for example, see Japanese Patent Application Publication Nos. H6-252042 and 2004-191833).

When a layer hardened or degenerated as described above (termed the degenerated layer hereafter) is formed on the surface of the photoresist film, it becomes difficult to remove the photoresist film when the implantation dose is high. A sulfuric acid-hydrogen peroxide mixture (SPM) at approximately 140° C. is extensively used in order to remove the photoresist film (to rinse the semiconductor substrate). However, the photoresist film may not be completely removed only by the SPM. Therefore, in order to remove the photoresist film used as a mask in the ion implantation, the photoresist film is first removed by a down flow of isotropic oxygen plasma and then the semiconductor substrate is thoroughly rinsed with the SPM. In this way, the semiconductor substrate having no photoresist film residue is further processed.

In the general manufacturing process of a semiconductor device, the photoresist film removal procedure and concrete process conditions are not changed once they are determined. On the other hand, the degree of hardening or degeneration of the resin film including photoresist films is evaluated for the purpose of determining the photoresist film removal conditions. The resin film evaluation is performed as follows.

FIGS. 14A to 14E show cross-sectional views for explaining the extensively used prior art resin film evaluation method. As shown in FIG. 14A, a desired film 102 such as a silicon oxide film and a photoresist film 103 are formed on a silicon substrate 101 in this order from the bottom. Then, as shown in FIG. 14B, the photoresist film 103 is exposed to exposure light 105 such as an ultraviolet, electron, or X ray via a reticle 104 having a desired pattern. The exposed photoresist film 103 is developed, rinsed with purified water, and post-baked to have the photoresist film 103 patterned as shown in FIG. 14C. Subsequently, as shown in FIG. 14D, ions 106 such as phosphorus, boron, or arsenic are implanted in the semiconductor substrate 101 by ion implantation using the pattern as a mask. Here, the surface layer of the photoresist film 103 where the ions 106 are implanted forms a degenerated layer 112 of which the molecular structure is different from that of the deep part. Then, the above described oxygen plasma treatment and SPM rinsing are performed to remove the photoresist film 103 as shown in FIG. 14E.

After the rinsing, the photoresist-removed surface is irradiated with a laser beam 110 and light reflected by resist residues 111 (or light scattered by the resist residues 111) is detected to determine a particle count. The particle count determined in this way is an indicator of the degrees of hardening or degeneration of the degenerated layer 112 formed on the surface of the photoresist film 103 provided that the photoresist film 103 is removed under given conditions. When the ion implantation is performed under given conditions, the particle count is an indicator of the resist removal ability of the removal conditions applied to the photoresist film 103 including the degenerated layer 112. In this way, the degrees of hardening or degeneration and removal property of a resin film can be evaluated.

The above evaluation method is similarly applicable where ion implantation shown in FIG. 14D is replaced with dry etching such as plasma etching. In such a case, the degree of hardening or degeneration of the degenerated layer formed in the surface layer of the photoresist film 103 as a result of exposure to etching gas plasma and the removal property of the plasma-etched photoresist film 103 can be evaluated based on the particle count.

In the manufacturing process of a semiconductor integrated circuit device, the removal of resin films such as photoresist films is checked by the above described evaluation method usually on an irregular basis if it is checked. In some cases, the shrinkage of the resist in association with the formation of a degenerated layer is determined by measuring an SEM (scanning electron microscopy) image for evaluating the degree of degeneration during the dry etching.

SUMMARY OF THE INVENTION

In recent semiconductor integrated circuit devices having semiconductor elements with finer patterns, impurity regions having a shallow pn junction are formed on a silicon substrate and the interlayer insulating films of a multilayer wiring structure tend to have a low dielectric constant (low-k). Therefore, when the photoresist film is removed by the oxygen plasma treatment and SPM rinsing as described above, the following problems become apparent.

When the photoresist film used as an ion implantation mask for forming an impurity region having a shallow junction is treated with oxygen plasma for removal, the surface of the ion-implanted region of the silicon substrate is exposed to oxygen plasma. FIGS. 15A and 15B are cross-sectional views showing that oxygen plasma treatment has effects on an n-channel transistor and a p-channel transistor formed in the process of CMOS (Complementary Metal Oxide Semiconductor). The n-channel transistor is illustrated on a right side and the p-channel transistor is illustrated on a left side in FIGS. 15A and 15B. Further, FIGS. 15A and 15B illustrate a process for forming an extension region of the p-channel transistor.

As shown in FIG. 15A, the p-channel transistor and the n-channel transistor are formed on a surface region of a semiconductor substrate 101 separated by an element isolation insulating film 151. The p-channel transistor is provided with a gate electrode 154a formed on an n-type well layer 152a with a gate insulating film 153a therebetween. The n-channel transistor is provided with a gate electrode 154b on a p-type well layer 152b with a gate insulating film 153b therebetween.

When the extension region in the p-channel transistor is formed, a resist pattern 159b which covers a formation region of the n-channel transistor is formed on the semiconductor substrate 101. In this state, p-type impurity ions are implanted, and p-type extension regions 156a are formed on both sides of the gate electrode 154a on the surface of the semiconductor substrate 101.

Next, the resist pattern 159b is removed. In this case, since a degenerated layer is formed in the surface portion of the resist pattern 159b, oxygen plasma treatment is applied. The p-type extension region 156a is exposed to oxygen plasma during the oxygen plasma treatment. Therefore, as shown in FIG. 15B, an ultrathin silicon oxide film 160a with several nm in thickness is formed on the surface of the p-type extension region 156a which reduces the thickness of the p-type extension region 156a. Consequently, the p-type extension region 156a has an increased sheet resistance. When the resist pattern 159b is removed in the process of oxygen plasma treatment, the surface of the semiconductor substrate 101 on both sides of the gate electrode 154b in the n-channel transistor is exposed to oxygen plasma. Therefore, silicon oxide films 160b are formed as well on both sides of the gate electrode 154b on the surfaces of the semiconductor substrate 101. The silicon oxide films 160b prevent ion from entering the semiconductor substrate 101 when ion implantation is performed to form the extension region of the n-channel transistor and the like, which is performed later on. As a result, it is impossible to form desired impurity regions in the semiconductor substrate 101.

When the extension region in the n-channel transistor is formed, similarly, a resist pattern to cover a formation region of the p-channel transistor is formed. When the oxygen plasma treatment is applied in order to remove this resist pattern, the silicon oxide film is formed on the surface of the semiconductor substrate 101. In this case, since ion species to be implanted is different, a state of the degenerated layer formed in the surface portion of the resist pattern is different from which formed in the surface portion of the resist pattern 159b. Thus, a thickness of the silicon oxide films on the extension region differs between in the p-channel transistor formation region and in the n-type transistor formation region. Therefore, as a result, that causes a problem that an electrical characteristic balance between the p-channel transistor and the n-type transistor will be lost.

On the other hand, when the photoresist film formed on a low-k (low dielectric constant) film as an etching mask is treated with oxygen plasma for removal, the low density low-k film is damaged and etched by the oxygen plasma. If such phenomenon occurs on the low-k film exposed in the region etched using the photoresist film as a mask, the etched region has a modified pattern. Alternatively, if such phenomenon occurs on the low-k film to be covered with the photoresist film, the interlayer low-k film has reduced thickness.

The above problems have caused unignorable influences on electric properties and their fluctuation of the semiconductor integrated circuit devices as the finer patterns are produced.

The chamber and members therein of an ashing apparatus used for oxygen plasma treatment are made of metals such as Al or an alloy including Fe. Therefore, the semiconductor substrate is contaminated with metals during the oxygen plasma treatment. If much finer patterns are created in the future, such metal-contamination to the semiconductor substrate should strictly be reduced in the semiconductor device manufacturing process.

As a measure to reduce the occurrence of the above problems, the oxygen plasma treatment time is reduced to the extent that the resist residue does not occur. As described above, the oxygen plasma treatment is used for effectively removing the surface layer (termed the degenerated layer hereafter) of a photoresist film that is hardened or degenerated. Therefore, at present, the oxygen plasma treatment is performed under conditions sufficient for complete removal of the degenerated layer. The conditions are not optimized for preventing excessive removal. Therefore, there is enough room for the oxygen plasma treatment time to be shortened so as to reduce the occurrence of the above problems. In order to optimize the oxygen plasma treatment, the formation of the degenerated layer (the degrees of hardening or degeneration) should quantitatively be evaluated.

However, the prior art evaluation of the degenerated layer uses the resist residue count as described above. Therefore, it is difficult to precisely know the state of hardening or degeneration within the degeneration layer. Even with the measurement of the shrinkage of the resist pattern for evaluation of the degenerated layer, it is also difficult to precisely know the state of hardening or degeneration within the degeneration layer. This is because the shrinkage of the resist pattern is caused not only by the degenerated layer but also by the ultraviolet irradiation to the resist pattern to harden the resist pattern before the etching. An additional problem is that it is difficult to determine the deformation rate due to shrinkage in thick photoresist films such as photoresist films used as a mask for CCD (charge coupled device) image sensors compared to thin resist films.

The above methods have the disadvantage that requires time and cost because of the degenerated layer is evaluated by measuring an indicator, such as the particle count and the like, of the result of the treated semiconductor substrate. The tendency for the photoresist film to form a degenerated layer also depends on the type of the photoresist film besides the ion implantation or dry etching conditions. This makes the experiments for the evaluation complicated. In other words, there is no effective method of evaluating the degenerated layer in an attempt to optimize the oxygen plasma treatment conditions according to the formation of the degenerated layer.

In the future, in the manufacturing process of the semiconductor integrated circuit device having much finer patterns, in removing the photoresist film, it is required to prevent occurrence of the resist residue (the particles), formation of the silicon oxide films on the surface of the semiconductor substrate in the oxygen plasma treatment of the photoresist film, metal-contamination to the semiconductor substrate and etching to the low-k film. Otherwise, manufacturing yields are severely decreased. Therefore, it is desired that technologies to easily evaluate the degenerated layer in short time and to determine the degree of achievement of a treatment applied to the semiconductor substrate, for example, whether or not particles are occurred, according to the result of the evaluation.

In view of the above, the purpose of the present invention is to provide a resin film evaluation method for evaluating the degenerated layer formed on the surface of a resin film such as a photoresist by charged energetic particles such as implantation ions in a simple and highly accurate manner and method for manufacturing a semiconductor device applying the resin film evaluation method.

In order to achieve the above purpose, the present invention uses the following technical means. In a resin film evaluation method of the present invention, first, an evaluation substrate having a resin film formed on an insulating layer with an opening in which the surface of the insulating layer is exposed is irradiated with charged energetic particles. Then, the surface potentials of the evaluation substrate irradiated with the charged energetic particles are measured. Based on the measurements, the difference in surface potential between the resin film and the insulating film exposed in the opening is obtained. Then, a physical quantity which varies in response to an achievement of a given treatment performed on the resin film irradiated with the charged energetic particles is estimated based on the difference in surface potential. Here, the given treatment is any treatment such as a removal process of the resin film that is performed after the irradiation with charged energetic particles. For example, if the given treatment is a removal process of the resin film, the physical quantity is a resin film residue count and the like.

In addition to the above configuration, it can be determined whether or not the estimated physical quantity is within a predetermined allowable range, whereby it is determined whether or not the material of the resin film, irradiation conditions of the charged energetic particles, or treatment conditions of the given treatment for the resin film are appropriate. Alternatively, it can be determined whether or not the difference in surface potential is within a range of differences in potential corresponding to the above allowable range, whereby it is determined whether or not the material of the resin film, irradiation conditions of the charged energetic particles, or treatment conditions of the given treatment for the resin film are appropriate.

In another resin film evaluation method of the present invention, first, multiple substrates, each of which has a resin film on an insulating layer of a given thickness with a fixed area of an opening wherein the surface of the insulating layer is exposed, are irradiated with charged energetic particles at different irradiation doses, respectively. Then, the surface potentials of the insulating films exposed in the opening of the each substrate irradiated with the charged energetic particles are measured and the relationship between the surface potential and the charged energetic particles irradiation dose is obtained. Based on the relationship, the charged energetic particles irradiation dose leading to the critical potential which is the maximum surface potential of the insulating film exposed in the opening is obtained. Based on the critical potential or the charged energetic particles irradiation dose corresponding to the critical potential, it is determined whether or not charge accumulated in the insulating film due to the charged energetic particles flows through the insulating film at a given charged energetic particles irradiation dose.

In a further other resin film evaluation method of the present invention, multiple substrates each having one of multiple resin films of different constituents formed on an insulating layer with an opening in which the surface of the insulating layer is exposed are irradiated with charged energetic particles under a given condition. Then, the surface potentials of the multiple substrates irradiated with the charged energetic particles are measured. Based on the measurements, the differences in surface potential between the resin film and the insulating film exposed in the opening on the each substrate are obtained. The differences in surface potential are compared, whereby the degeneration progresses of the degenerated layers that occur in the resin films when the each substrate is irradiated with the charged energetic particles are compared.

In the above configuration, it is preferable that the difference in surface potential is the difference in surface potential between the resin film and the insulating film in the area including a edge of the opening. The given treatment performed on the resin film can be a removal process of the resin film and the physical quantity can be the residue count or residue density of the resin film after the resin film removal process. In such a case, the resin film removal process can be a chemical solution removal process.

In the above configuration, the charged energetic particles can be implantation ions and the resin film can be a photoresist. Alternatively, the charged energetic particles can be particles in plasma and the resin film can be a photoresist. In such a case, the insulating film can be a silicon oxide film.

When the charged energetic particles are implantation ions, the insulating film preferably at least has a thickness of $Rp1+3\Delta Rp1$ or larger where $Rp1$ is the projected range of the implanted ions in the insulating film and $\Delta Rp1$ is the standard deviation of the projected range $Rp1$. Furthermore, the photoresist preferably at least has a thickness of $Rp2+3\Delta Rp2$ or larger where $Rp2$ is the projected range of the implanted ions in the photoresist and $\Delta Rp2$ is the standard deviation of the projected range $Rp2$.

Additionally, it is preferable that the area ratio of the resin film to the substrate is 90% or higher. When the charged energetic particles are implantation ions and the resin film is a photoresist, the implantation dose of ion implantation is preferably $1 \times 10^{10}/cm^2$ to $1 \times 10^{14}/cm^2$.

In the meantime, from another point of view, the present invention provides a method for manufacturing a semiconductor device having impurity regions formed by ion implantation. Namely, in a method for manufacturing a semiconductor device in accordance with the present invention, a first resist pattern is firstly formed on a semiconductor substrate. Next, by ion implantation using the first resist pattern as a mask, an impurity region is formed on the semiconductor substrate. Then, ion implantation of the same ion implantation condition as previously is performed on an evaluation substrate on which a second resist pattern composed of the same material as the first resist pattern having an opening in which the insulating film is exposed on the insulating film formed on a substrate. Surface potentials on the second resist pattern and the insulating film on the evaluation substrate are measured. Based on the measured surface potentials on the second resist pattern and the insulating film, it is determined whether or not removal of the first resist pattern is allowable based on the given resist removal condition. When it is determined as not allowable, the resist removal condition is changed conforming to enable to be removed even by a difference in the measured surface potential between the second resist pattern and the insulating film, and thereby the first resist pattern is removed on the changed resist removal condition. When it is determined as allowable, the first resist pattern is removed on the resist removal condition.

Further, whether or not the second resist pattern is removable is determined by whether or not the resist residue count or the resist residue density after the removal of the resist pattern which corresponds to the difference in the measured surface potential between the second resist pattern and the insulating firm is within an allowable range in the manufacturing process of the semiconductor device.

In the method for manufacturing a semiconductor device, the implantation dose of ion implantation can be $1 \times 10^{10}/cm^2$ to $3 \times 10^{14}/cm^2$. Further, the resist pattern is preferably removed by using only chemical solution not using an oxygen plasma treatment.

The resin film evaluation method of the present invention allows for quantitative evaluation of a resin film such as a photoresist for tendency to form a degenerated layer during the ion implantation or dry etching. Then, the electrical charging level of a resin film by charged energetic particles, etching resistance of the resin film, and removal property of the resin film after the ion implantation or dry etching can be estimated. Consequently, the degrees of hardening or degeneration in the surface layer of a resin film during the ion implantation or dry etching can easily be known. Furthermore, resin films that are difficult to be charged up during the ion implantation or dry etching or resin films that are easily removed after the treatment can easily be found. It is possible to find a resin film that can be removed after the treatment only by a chemical solution without the oxygen plasma treatment. Alternatively, even if the oxygen plasma treatment is performed, the treatment time can be reduced to the minimum necessity.

The evaluation method of the present invention also allows for evaluation on the possibility of dielectric breakdown in the insulating film during the treatment under given conditions including device structures and ion implantation or plasma etching conditions.

The evaluation method of the present invention is applicable regardless of the resin film thickness and easily applicable to the structures that are difficult to evaluate in the prior art such as CCD image sensors.

According to the method for manufacturing a semiconductor device of the present invention, it can be easily determined in a short time whether or not the resist pattern on which the degeneration layer is formed by the ion implantation is removable on the predetermined resist removal conditions. Further, the resist pattern is reliably removed without generating particles.

The foregoing and other objects, features, aspects and advantages of the present invention will become more apparent from the following detailed description of the present invention when taken in conjunction with the accompanying drawings.

DETAILED DESCRIPTION OF PREFERRED EMBODIMENTS

The resin film evaluation method of the present invention is described hereafter with reference to the drawings. The resin film evaluation method of the present invention uses an evaluation substrate prepared by forming an insulating film on a substrate and forming a resin film on the insulating film with an opening in which the insulating film is partly exposed. The evaluation substrate is irradiated with charged energetic particles for example by ion implantation or plasma exposure under given conditions to form a degenerated layer in the area including the resin film surface. The surface potentials in the resin film area and in the exposed insulating film area on the evaluation substrate obtained in this way are measured and the degenerated layer of the resin film is evaluated based on the surface potential measurements.

FIGS. 1A to 1D are a series of cross-sectional views showing from the preparation of an evaluation substrate to the surface potential measurement according to an embodiment of the resin film evaluation method of the present invention. Here, the resin film is irradiated with charged energetic particles by ion implantation.

Figure 1A:
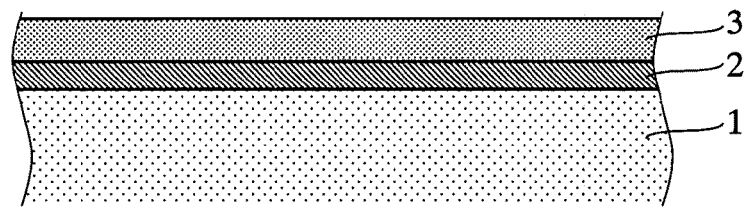
FIGS. 1A to 1D are a series of cross-sectional views showing from the preparation of an evaluation substrate to the surface potential measurement according to an embodiment of the present invention.

First, as shown in FIG. 1A, a silicon oxide film 2 as an insulating film is formed on a silicon substrate 1 for example by thermal oxidation or CVD (chemical vapor deposition). The insulating film can be a silicon nitride film or a metal oxide dielectric film such as aluminum oxide, tantalum oxide, and hafnium oxide films. The insulating film can be a laminated film of a proper combination of these films. A photoresist film 3 having a thickness of approximately 1 μm is formed as a resin film to be evaluated on the silicon oxide film 2.

Figure 1B:
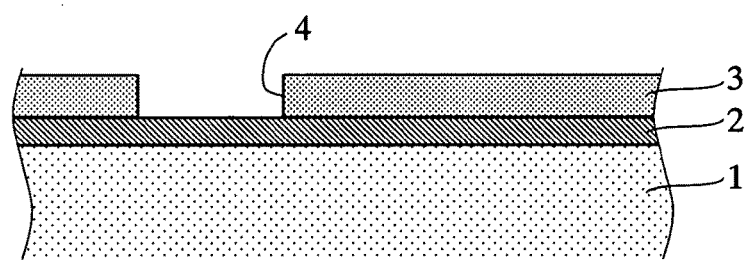

Then, as shown in FIG. 1B, the photoresist film 3 is exposed to exposure light of wavelengths to which the photoresist film 3 is photosensitive (ultraviolet, electron, or X ray) via a reticle having a desired pattern (not shown). The exposed photoresist film 3 is developed, rinsed with purified water, and post-baked to form an opening 4. The opening 4 is not a small opening such as an element pattern generally used in a semiconductor integrated circuit device. For example, when the silicon substrate 1 has a diameter of 200 nm, the opening 4 is a square of 5 mm to 20 mm on a side or an opening having an area equivalent to this square. It is preferable that the opening 4 is formed so that the photoresist film 3 occupies approximately 90% or more of the area of the silicon substrate 1. As described above, the dimensional accuracy is not required; therefore, the opening 4 can be formed by exposure without a reticle.

Figure 1C:
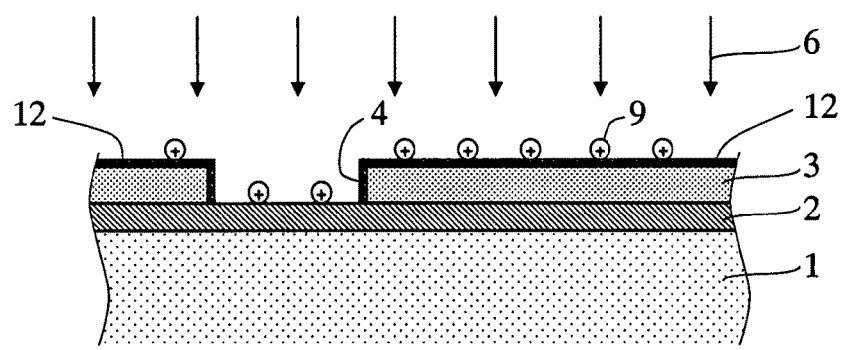

Then, as shown in FIG. 1C, the silicon substrate 1 is placed in an ion implantation apparatus and impurity ions such as phosphorus, boron, and arsenic are implanted in the silicon substrate 1. Consequently, the implantation ion 6 is directly implanted in the surface layer of the photoresist film 3 and a degenerated layer 12 is formed by ion bombardment. Meanwhile, charge 9 accumulates on the surface of the photoresist film 3 and on the surface of the silicon oxide film exposed at the bottom of the opening 4.

Figure 1D:
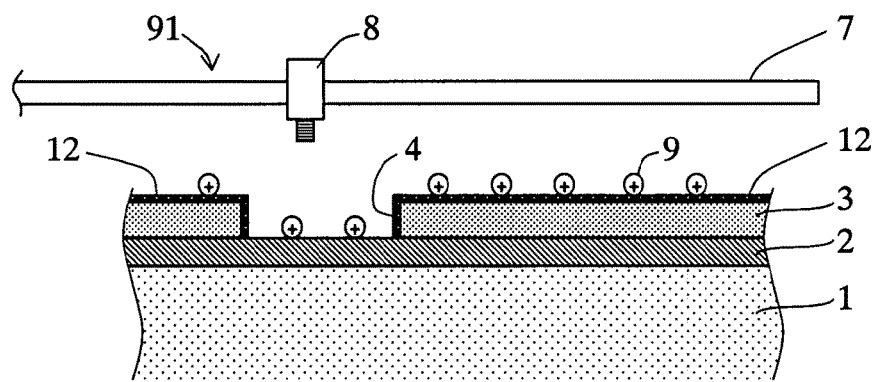

After the ion implantation is completed, the treated evaluation substrate is removed from the ion implantation apparatus. The treated evaluation substrate is placed on the substrate support (stage) of a surface potential measuring apparatus, the substrate support consisting of a conductive material such as a metal and being connected to a ground potential. The surface potential corresponding to the charge 9 accumulated on the evaluation substrate is measured. As shown in FIG. 1D, the surface potential is measured using a surface potential measuring apparatus 91 having a surface potential measuring sensor 8 positioned, for example, as close as approximately 0.5 mm to 3 mm, more preferably approximately 1 mm to 1.5 mm, to the surface of the photoresist film 3. The sensor 8 is movable along a guide 7 provided nearly in parallel to the surface of the evaluation substrate from one end to the other of the silicon substrate 1 via above the opening 4. The sensor 8 measures the surface potential of the evaluation substrate at horizontal intervals of 1 mm to 2 mm along the guide 7. The guide 7 can be positioned, for example, along a diameter passing through the center of the evaluation substrate.

The above surface potential measurement must be conducted while the surface charge distribution after the ion implantation is maintained before the charge accumulated on the silicon oxide film 2 and photoresist film 3 is reduced because of runoff or neutralization. The surface potential should be measured within 24 hours after the evaluation substrate is removed from the ion implantation apparatus. Particularly, it is desirable that the surface potential is measured within 2 hours after the evaluation substrate is removed from the ion implantation apparatus. In such a case, the charge loss is less than 1% and there is no influence on the surface potential measurements. When the evaluation substrate is removed from the ion implantation apparatus, it is desirable that the evaluation substrate is held on the back by arms or vacuum tweezers of the transfer unit so that nothing makes contact with the evaluation substrate surface on which charge is accumulated.

How the degeneration layer 12 formed on the surface of the photoresist film 3 is evaluated by the evaluation method shown in FIGS. 1A to 1D is described hereafter using concrete embodiments.

Figure 2:
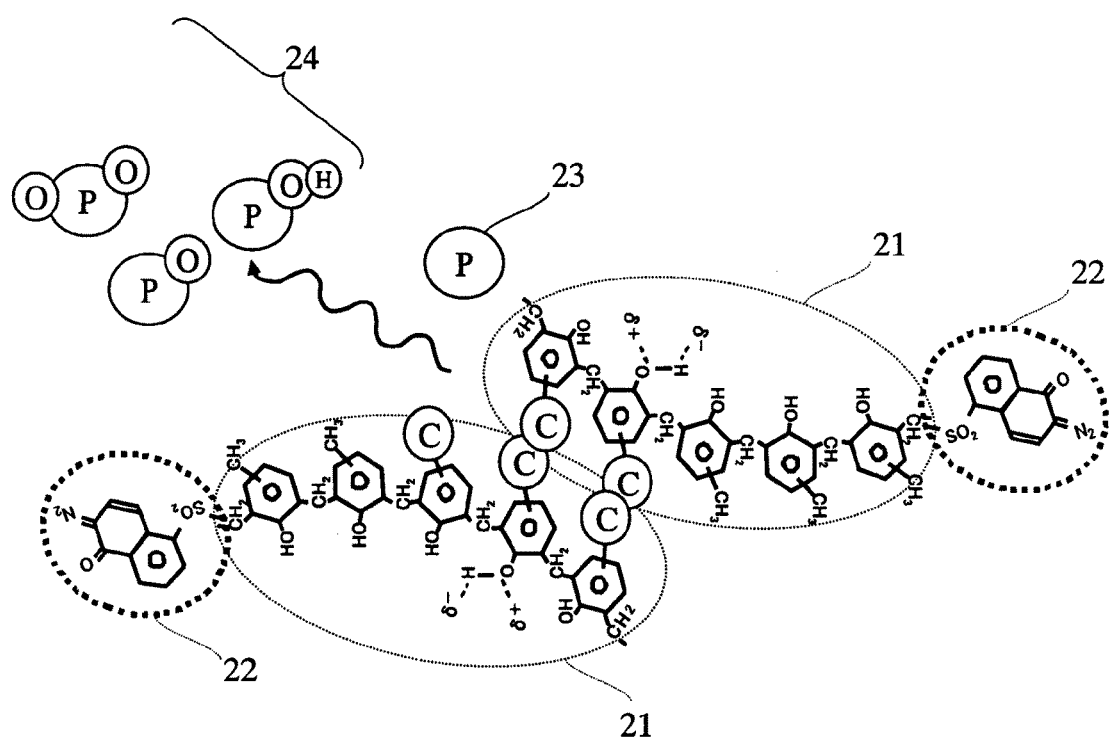
FIG. 2 is a schematic illustration for explaining a mechanism of formation of a degenerated layer.

FIG. 2 is a schematic illustration showing a mechanism of formation of the degenerated layer 12 on the photoresist film 3 through ion implantation. FIG. 2 shows an i-line photolithographic photoresist film 3 consisting of a naphthoquinonediazide photosensitive agent 22 in a novolak resin 21 base and having phosphorus ions ($P^+$) 23 implanted.

As shown in FIG. 2, after the ions are implanted, the internal bonds of the polymer (novolak resin 21) constituting the photoresist film 3 are broken by the ion bombardment of the implanted phosphorus ions 23, whereby carbon (C) radicals are produced. The radicals are unstable. Therefore, the produced carbon radicals rebind to nearby impurities or carbons. Meanwhile, the implanted phosphorus ions 23 react with the oxygen of the novolak resin 21 (deoxidation) and evaporate as a gas 24 such as P—O. Such cross-linkage and deoxidation leads to the formation of a carbon-rich degenerated layer 12. Here, when less cross-linkage occurs and there is no significant change in the photoresist molecular structure before and after the ion implantation, hardening is observed.

Figure 3:
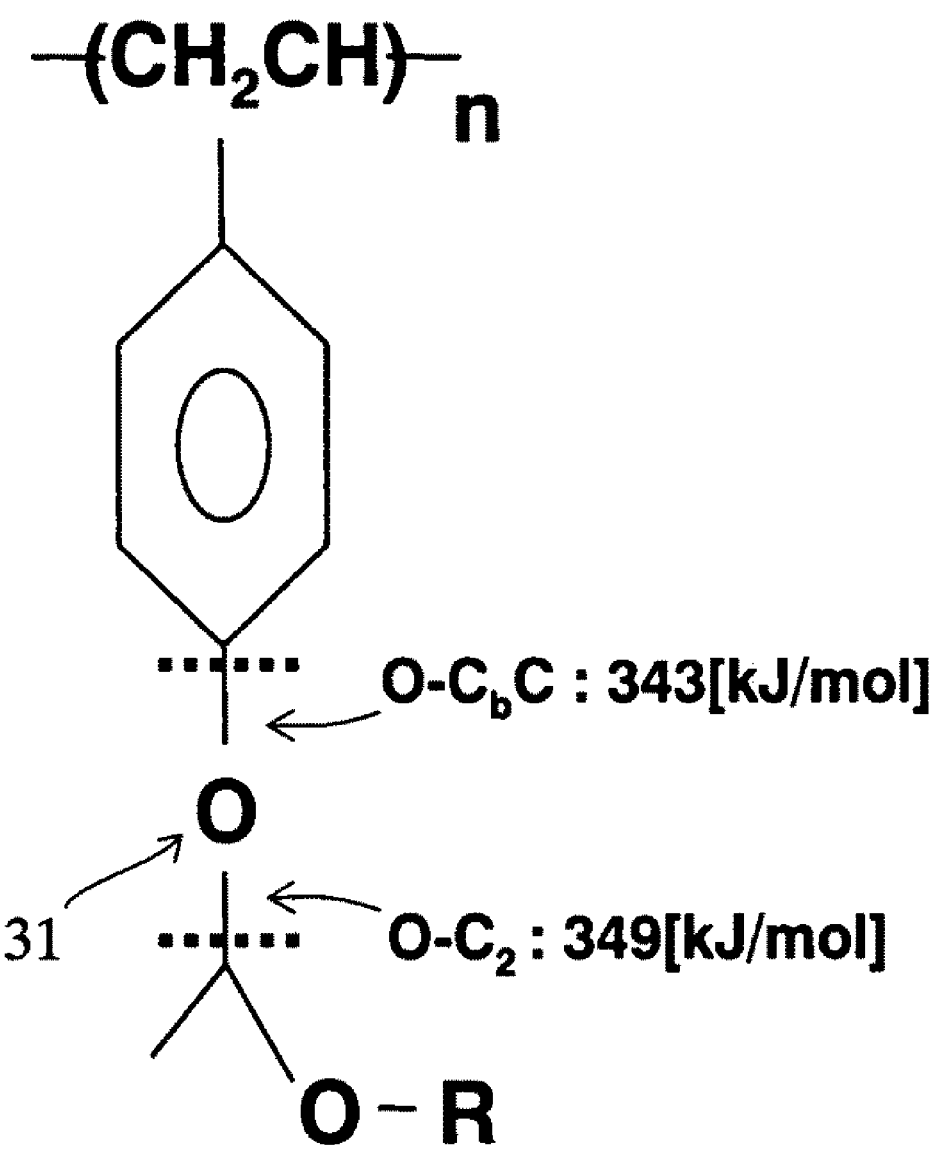
FIG. 3 is a schematic illustration for explaining a mechanism of formation of a degenerated layer.

FIG. 3 is an illustration for explaining another mechanism of formation of the degenerated layer 12 on the surface of the photoresist film 3 through ion implantation. FIG. 3 shows the molecular structure around a protective group of an acetal KrF excimer lithographic photoresist. In this case, as shown in FIG. 3, the bond energies of an oxygen atom 31 in the middle of FIG. 3 are 343 kJ/mol (O—$C_b$C) and 349 kJ/mol (O—$C_2$), which are much lower than the bond energies of the other parts within the photoresist material. Therefore, the bonds are easily broken by ion bombardment during the ion implantation. In this case, the carbon that has lost the bond to oxygen is crosslinked. In this way, the polymer structure is degenerated differently depending on resin materials.

The degenerated layer 12 presumably has a reduced electric resistance as an increasing number of carbon bonds are formed compared to the initial insulating state. As the carbon-related reactions further occur, a so called carbonization is observed where most of the internal bonds of the resist are broken and the degenerated layer 12 becomes considerably highly conductive. In this state, the charge accumulated during the ion implantation moves between the photoresist film 3 and the silicon oxide film 2 exposed in the opening 4 on the evaluation substrate shown in FIG. 1D. Consequently, the surface potential distribution (the surface potential of the photoresist film 3 and the surface potential of the silicon oxide film 2) is changed. The surface potential distribution on the evaluation substrate is changed according to the conductivity (electric resistance) of the regenerated layer 12. Therefore, the degree of hardening or degeneration of the degenerated layer 12 can be known by evaluating the surface potential distribution on the evaluation substrate.

Figure 4:
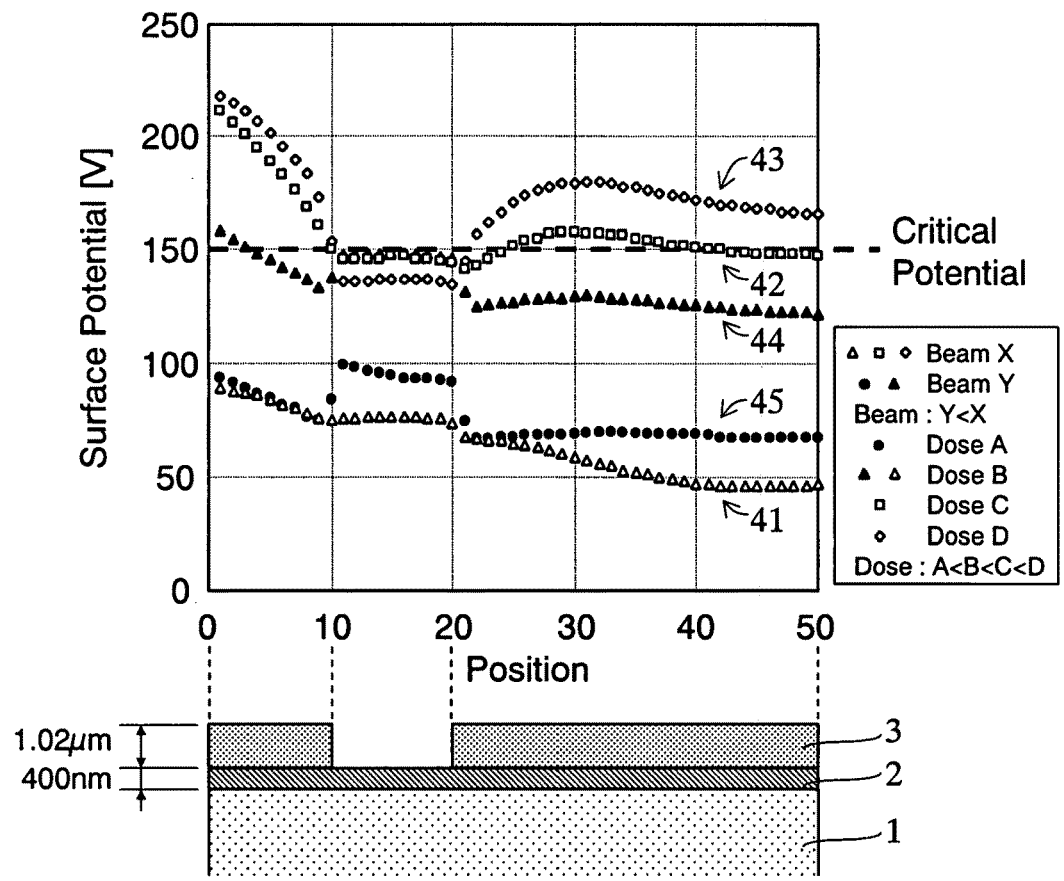
FIG. 4 is a graphical representation showing the surface potential measurements by way of example.
Figure 5:
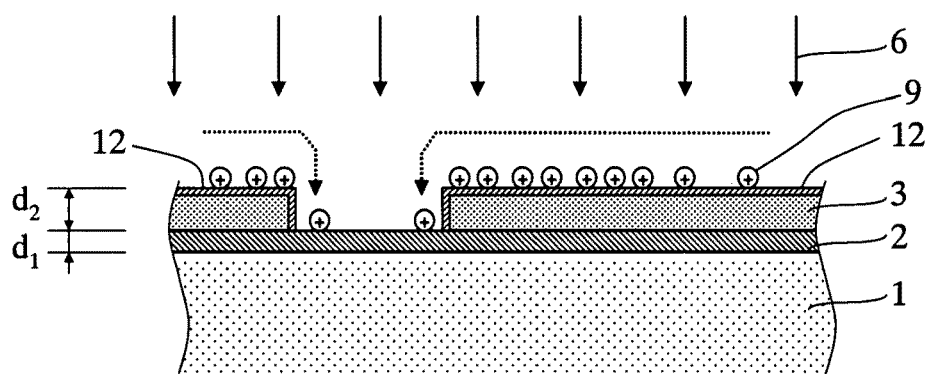
FIG. 5 is a cross-sectional view of the evaluation substrate from which the data shown in FIG. 4 are obtained.
Figure 6:
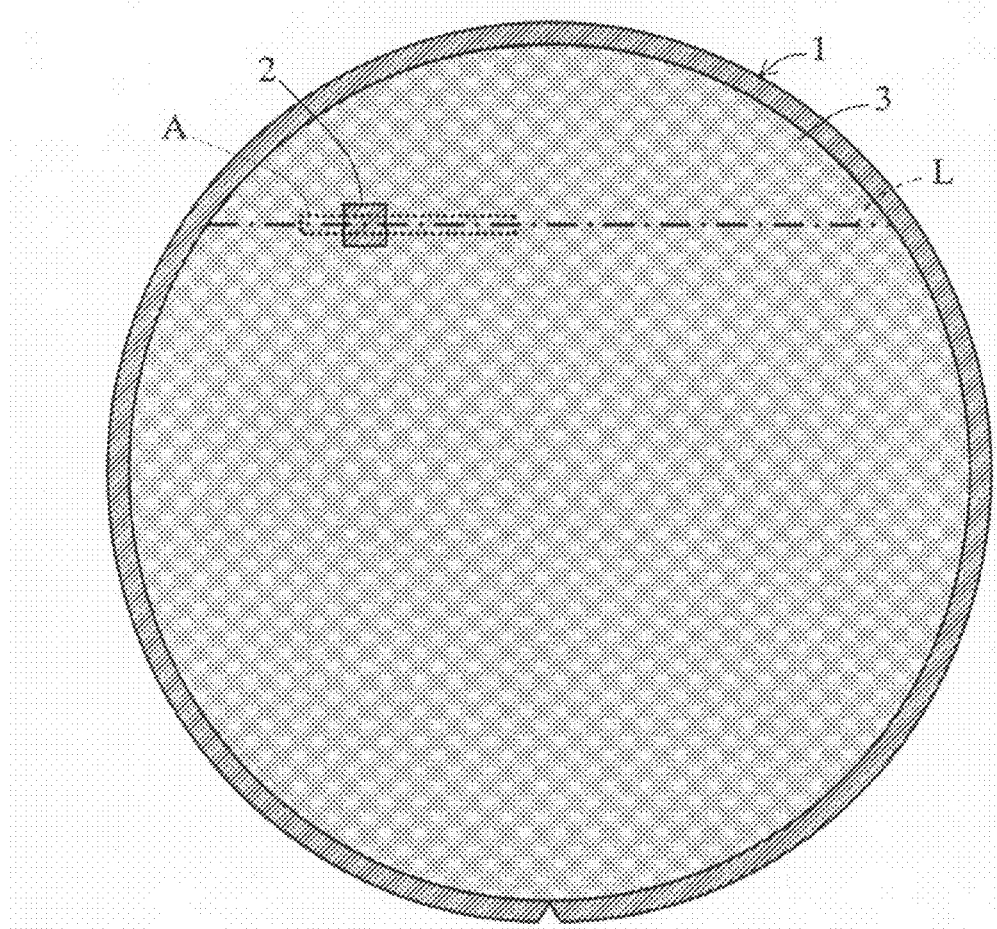
FIG. 6 is a top view of the evaluation substrate shown in FIG. 5.
Figure 7:
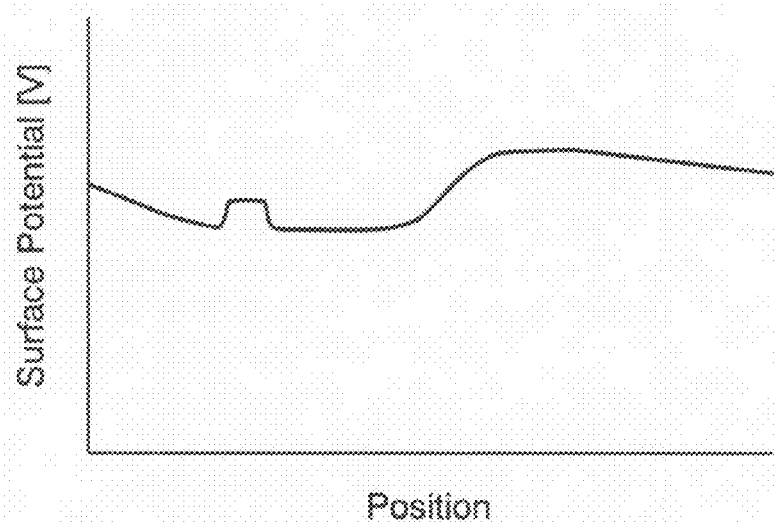
FIG. 7 is a graphical representation showing the surface potential distribution along line L shown in FIG. 6 by way of example.

FIG. 4 is a graphic representation showing the surface potential measurements of ion-implanted evaluation substrates by way of example. FIG. 5 is a cross-sectional view of the evaluation substrates from which the data shown in FIG. 4 are obtained. FIG. 6 is a top view of the evaluation substrate shown in FIG. 5. And, FIG. 7 is a graphical representation showing the surface potential distribution along line L shown in FIG. 6 by way of example.

As shown in FIG. 5, the evaluation substrate has a silicon substrate 1 on which a silicon oxide film 2 having a thickness $d_1$ of 400 nm and a photoresist film 3, having a thickness $d_2$ of 1.02 μm are formed. Here, the thickness $d_1$ of the silicon oxide film 2 satisfies $d_1 > Rp1 + 3\Delta Rp1$ where Rp1 is the projected range of ions implanted in the silicon oxide film 2 and $\Delta Rp1$ is the standard deviation of the projected range Rp1. The thickness $d_2$ of the photoresist film 3 satisfies $d_2 > Rp2 + 3\Delta Rp2$ where Rp2 is the projected range of ions implanted in the photoresist film 3 and $\Delta Rp2$ is the standard deviation of the projected range Rp2. Phosphorus ions are implanted throughout the evaluation substrate in the ion implantation. The accumulation of the charge 9 by the implanted ion 6 starts as soon as the degenerated layer 12 starts to form on the surface of the photoresist film 3.

As shown in FIG. 6, the evaluation substrate is provided with the silicon oxide film 2 on entire silicon substrate 1, and the photoresist film 3 is provided on the silicon oxide film 2 except for a peripheral area (5 mm). The silicon oxide film 2 is exposed in the opening with one side 10 mm provided on the photoresist film 3. The surface potential distribution as shown in FIG. 4 and the cross-sectional view as shown in FIG. 5 correspond to an area A on line L shown in FIG. 6.

FIG. 4 shows the surface potential measurements of the evaluation substrates in which phosphorus ions ($P^+$) are implanted under different ion implantation conditions. In FIG. 4, the horizontal axis corresponds to the surface potential measuring position and the vertical axis corresponds to the surface potential. The surface potentials on the silicon oxide film 2 are plotted in a range from 10 to 20 on the horizontal axis. The surface potentials on the photoresist film 3 are plotted in a range from 0 to 10 and a range from 20 and higher on the horizontal axis. Here, the area of the opening at the bottom of which the silicon oxide film is exposed is approximately 0.4% of the area covered with the photoresist film.

The evaluation substrates are subject to ion implantation under different implantation dose and beam (ion current value or dose rate) conditions. In FIG. 4, open triangle data 41, open square data 42, and open diamond data 43 are obtained by ion implantation under the same beam condition (Beam X). The ion implantation doses for the data 41 (implantation dose B: approximately $5 \times 10^{12}/cm^2$), data 42 (implantation dose C), data 41 (implantation dose D) satisfy the relationship B<C<D.

As understood from FIG. 4, the surface potential distribution on the evaluation substrate from the relatively low dose data 41 has an overall potential gradient; the surface potentials on the photoresist film 3 and silicon oxide film 2 are nearly continuous and not significantly different. Under this condition, the cross-linkage did not occur so much in the surface layer of the photoresist film 3 and the electric resistance in the surface layer (the degenerated layer 12) is not reduced so much. In this case, the photoresist film 3 and silicon oxide film 2 can be assumed to be the capacitive insulating film of a capacitor.

The area where the photoresist film 3 is present (termed the photoresist film area hereafter) is larger in thickness than the area where the silicon oxide film 2 is exposed (termed the silicon oxide film area hereafter). Therefore, the unit area capacitance of the photoresist film area is smaller than the unit area capacitance of the silicon oxide film area. Then, assuming that the accumulated charge quantities in these areas are equal, the photoresist film area must have a higher potential. However, in fact, secondary electrons (minus electric charge) released from the silicon oxide film 2 during the ion implantation are attracted to plus charge on the photoresist film 3 to lower the surface potential for keeping the potential equilibrium. Therefore, the surface potential of the photoresist film area presumably becomes nearly equal to the surface potential of the silicon oxide film area. As shown in FIG. 7, the surface potential on the photoresist film 3 apart to some extent from the opening of the photoresist film 3 is higher than the surface potential on the silicon oxide film area.

As understood from the data 42 in FIG. 4, as the implantation dose is increased, the surface potentials on the silicon oxide film 2 and photoresist film 3 are raised. The surface potential of the photoresist film area is raised at higher rates than the surface potential of the silicon oxide film area. Furthermore, as the implantation dose is increased (the data 43), the surface potential on the photoresist film area is further raised while the surface potential of the silicon oxide film area is lowered.

As described above, in the degenerated layer 12 of the photoresist film 3, oxygen in the photoresist film 3 is released by the implanted ion 6 and remaining carbons crosslink with each other, becoming conductive. This phenomenon occurs in the surface layer of the photoresist film 3. The underlying bulk part of the photoresist film 3 remains insulated. Therefore, the charge 9 accumulates in the conductive degenerated layer 12 in the photoresist film area. Such charge 9 presumably shifts to the silicon oxide film 2 via the sidewall of the degenerated layer 12 as shown in FIG. 5 when the degenerated layer 12 is deteriorated and conductivity is increased in the course of the ion implantation. Then, the potential distributions obtained by the data 42 and 43 shown in FIG. 4 suggest that some charge 9 in the photoresist film area flows into the silicon oxide film 2.

On the other hand, in the silicon oxide film area, the surface potential drops after it has reached the critical potential (approximately 150 V in FIG. 4). This is because the surface potential of the silicon oxide film 2 causes a large potential gradient in the silicon oxide film 2 so that the charge 9 partly flows to the silicon substrate 1 through the silicon oxide film 2 and does not accumulate in the silicon oxide film 2 more than a given quantity. The charge 9 on the photoresist film 3 continues to flow to the silicon oxide film area. Therefore, the surface potential on the silicon oxide film 2 is determined by the relative quantities of the charge leaking out through the silicon oxide film 2 and the charge flowing in from the photoresist film 3. As understood from the data 42 and 43 in FIG. 4, the surface potential on the silicon oxide film 2 is maximized at the implantation dose leading to the critical potential and then drops as the implantation dose is further increased.

In FIG. 4, filled triangle data 44 show the surface potential distribution obtained at the same implantation dose B as the open triangle data 41 and with a lower beam (smaller ion current value or dose rate, Beam Y) than the data 41. Filled circle data 45 show the surface potential distribution obtained with the same beam as the data 44 (Beam Y) and at a lower implantation dose A than the data 44.

As understood from the data 41 and 44, a lower beam produces an overall larger surface potential and the potential is higher in the silicon oxide area than in the photoresist film area. This is because, with the lower beam (Beam Y), a supply of secondary electrons released when ion collides with a platen and a carrier system, exposed in the periphery of the silicon substrate, is decreased as compared with the higher beam (Beam X). That is, the charge on the photoresist film 3 is hard to be neutralized due to the secondary electrons so that the surface potential becomes higher entirely. As understood from the data 44 and 45, the overall surface potential is lower as the implantation dose is reduced also at a lower beam.

Although the electric resistance in the surface layer of the photoresist film 3 (the degenerated layer 12) is hardly reduced at this implantation dose as described above, the charge 9 is barely flowing from the photoresist film area in the vicinity of the silicon oxide film area into the silicon oxide film area. In this case, as a result, the charge quantities flowing from the photoresist film area into the silicon oxide film area with the lower beam (data 44) become relatively larger than that flowing from the photoresist film area into the silicon oxide film area with the higher beam (data 41). Therefore, it is presumed that the surface potential is higher in the silicon oxide film area than in the photoresist film area with the lower beam (data 44).

According to the overall results described above, the surface potential is raised both on the silicon oxide film 2 and on the photoresist film 3 as the implantation dose is increased under a given dose rate (beam) condition. On the other hand, a rising of the surface potential is lower as the dose rate (beam) is increased under a given implantation dose condition.

Figure 8A:
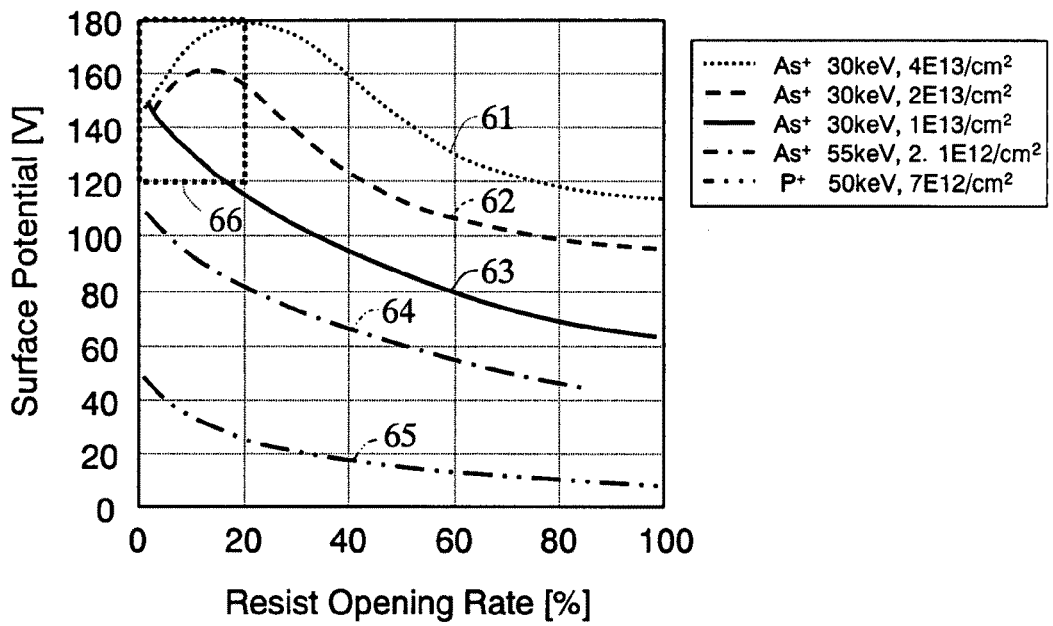
FIGS. 8A and 8B are graphical representations showing the relationship between the resist opening rate and the surface potential.
Figure 8B:
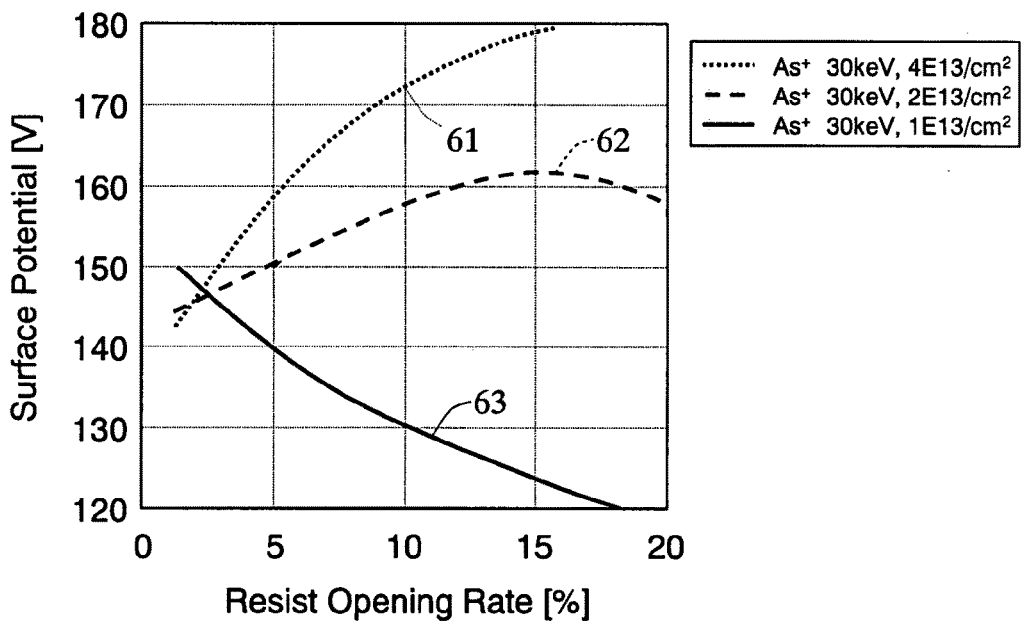

On the other hand, FIGS. 8A and 8B are graphical representations showing the dependency of the surface potential of the silicon oxide film 2 on the resist opening rate of the evaluation substrate having ions implanted under different ion implantation conditions. In FIGS. 8A and 8B, the horizontal axis corresponds to the resist opening rate and the vertical axis corresponds to the surface potential. Here, the evaluation substrate has one opening 4 in the photoresist film 3 for measuring the surface potential. The silicon oxide film 2 on the evaluation substrate has a thickness of approximately 400 nm. The opening rate is calculated by dividing the area of the opening 4 of the photoresist film 3 by the surface area of the silicon substrate 1. Therefore, the opening rate of 100% means that there is no photoresist film 3 on the silicon substrate 1.

In FIGS. 8A and 8B, dotted line data 61, broken line date 62, and solid line data 63 show the surface potentials when arsenic ions (As$^+$) are implanted at the same implantation energy (30 keV). The implantation doses for the data 61, 62, 63 are $4 \times 10^{13}/cm^2$, $2 \times 10^{13}/cm^2$, and $1 \times 10^{13}/cm^2$, respectively. Dash-dot line data 64 show the surface potential when arsenic ions (As$^+$) are implanted at an implantation energy of 55 keV and implantation dose of $2.1 \times 10^{12}/cm^2$. Dash-dot-dot line data 65 show the surface potential when phosphorus ions (P$^+$) are implanted at an implantation energy of 50 keV and implantation dose of $7 \times 10^{12}/cm^2$.

As understood from FIG. 8A, the surface potential varies depending on the implanted ion species. The surface potential is raised as the implantation dose is increased. Furthermore, the surface potential is raised as the resist opening rate is reduced from 100%. The surface potential is particularly high when the resist opening rate is approximately 10% or lower (the area occupancy of the photoresist film is approximately 10% or higher.) Therefore, if the surface potential is measured at a resist opening rate in this range, changes in the difference in surface potential in association with ion implantation conditions occur with improved sensitivity, whereby the degeneration degree of the degenerated layer 12 can easily be evaluated (particularly the data 63, 64, and 65).

The reason for the above behavior of the surface potential in association with the resist opening rate is presumably as follows. Charged energetic particles such as implantation ions cause cross-linkage of carbons or carbonization in the degenerated layer 12, gradually reducing the electric resistance. However, the absolute value of this electric resistance is approximately 10 orders higher than the resistance of the impurity region formed on the silicon substrate 1. Therefore, the charge 9 flowing in the opening 4 is presumably the charge 9 accumulated in the photoresist film 3 more or less within a certain distance from the edge of the opening 4. Then, in a case that the area of the opening 4 is reduced, the charge 9 accumulated in the silicon oxide film area has a relatively large density in response to reduction in the area of the opening 4. As a result, the surface potential in the silicon oxide film is raised.

The surface potential is maximized at a specific resist opening rate within the range of small resist opening rates under the high implantation dose conditions in FIG. 8A (the data 61 and 62). This is presumably because where the surface potential is maximized is where it has reached the above described critical potential. The charge 9 presumably flows to the silicon substrate 1 through the silicon oxide film 2 when the resist opening rate is lower than the resist opening rate at which the surface potential is maximized.

FIG. 8B is an enlarged view of the part 66 enclosed by dotted line in FIG. 8A. As shown in FIG. 8B, the low implantation dose data 63 show the surface potential monotonically raised as the resist opening rate is reduced even in a range of resist opening rates of 5% and lower because the amount of charge accumulated is small and the photoresist film 3 is not so much degenerated. On the other hand, the high implantation dose data 61 and 62 show the surface potential lowered as the resist opening rate is reduced after it has reached the critical potential. The higher implantation dose data 61 reaches the critical potential at a higher resist opening rate than the implantation dose data 62. In other words, at the same resist opening rate, the low implantation dose data 63 indicates that the charge 9 does not flow through the silicon oxide film 2 while the data 61 and 62 indicate that the charge 9 flows through the silicon oxide film 2. This is consistent with the behavior of the charge 9 on the evaluation substrate described with reference to FIG. 4.

(First Evaluation Method Using Surface Potential Measurement)

As described with reference to FIGS. 4, 8A and 8B, the phenomenon in the resin and insulating films caused by charge can be evaluated by calculating the difference in surface potential between the resin film such as a photoresist film and the insulating film such as a silicon oxide film. Furthermore, the degree of degeneration in the surface layer of the resin film caused by irradiation with charged energetic particles can be evaluated by calculating the difference in surface potential between the resin film and the insulating film.

Figure 9:
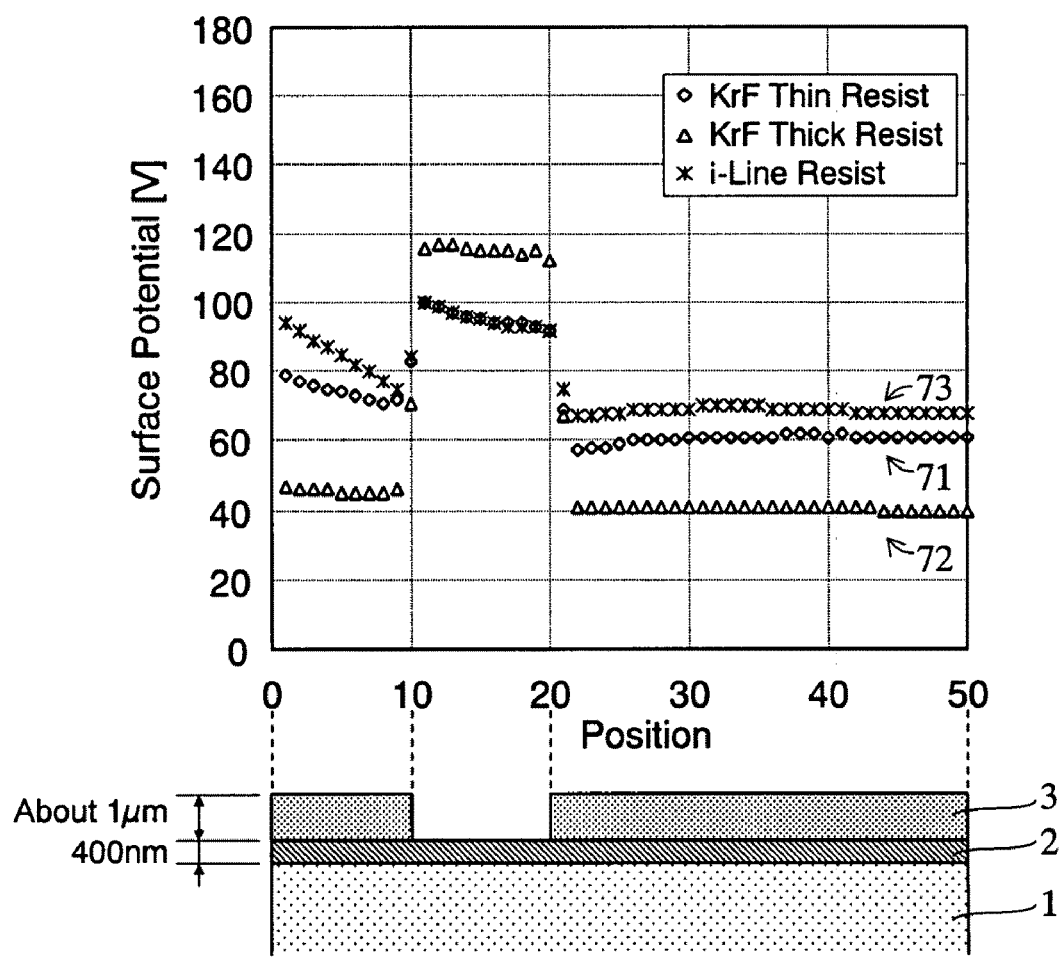
FIG. 9 is a graphical representation showing the relationship between the resist species and the surface potential.

FIG. 9 is a graphical representation showing the surface potential measurements of the evaluation substrates having resin films of different constituent materials and ions implanted. As remarked in FIG. 9, the evaluation substrate has a silicon substrate 1 on which a silicon oxide film 2 having a thickness of approximately 400 nm and a photoresist film 3 having a thickness of approximately 1 µm are deposited. Phosphorus ions (P$^+$) are implanted in the entire surface of the evaluation substrate at an implantation energy of 40 keV and implantation dose of $6 \times 10^{12}/cm^2$.

Diamond data 71 in FIG. 9 represent a KrF chemically amplified resist used in a relatively small thickness (termed the KrF thin resist hereafter) as the photoresist film 3. Triangle data 72 in FIG. 9 represent a KrF chemically amplified resist used in a relatively large thickness (termed the KrF thick resist hereafter) as the photoresist film 3. The KrF thick resist is made of a different material from the KrF thin resist. Asterisk data 73 in FIG. 9 represent an i-line photolithographic photoresist (termed the i-line resist hereafter) as the photoresist film 3. In FIG. 9, the horizontal axis corresponds to the surface potential measuring position and the vertical axis corresponds to the surface potential. The silicon oxide film area extends from 10 to 20 on the horizontal axis. The photoresist film area extends from 0 to 10 and 20 and higher on the horizontal axis.

As understood from FIG. 9, the difference in surface potential between the photoresist film area and the silicon oxide film area varies depending on photoresist film species. In other words, the difference in surface potential between the two areas is increased in the order of the i-line resist (data 73), KrF thin resist (data 71), and KrF thick resist (data 72).

From the above described resist degeneration process, it is easily assumed that the degrees of degeneration or polymer cross-linkage in the degeneration layers 12 of the above resist materials at the same ion implantation rate are increased in the above order. Consequently, it is understood that both KrF chemically amplified resists are less resistant to charged particle beam irradiation than the i-line resist. This is because the KrF resist has highly reactive to exposure compared to the i-line resist for high pattern resolution. The KrF thick resist used in a relatively large thickness is more sensitive to exposure than the KrF thin resist to allow for fine pattern formation in spite of the thickness. Therefore, the degree of degeneration in the degenerated layer 12 is increased. The results of FIG. 9 reflect those characteristics.

As understood from the data 71 and 73 in FIG. 9, the difference in surface potential between the silicon oxide film area and the photoresist film area is not always constant. Then, in order to obtain a quantitative difference in surface potential between the two areas, it is desirable to obtain the difference in potential at the border between the photoresist film 3 and the silicon oxide film 2 where the difference in potential abruptly changes. When the differences in potential at the right and left borders are different as of the data 71 in FIG. 9, it is desirable to use the larger difference in potential. However, the difference in surface potential can be an average difference in potential of the differences in potential at the right and left boarders or a total difference in potential of the differences in potential at the right and left boarders.

Figure 10:
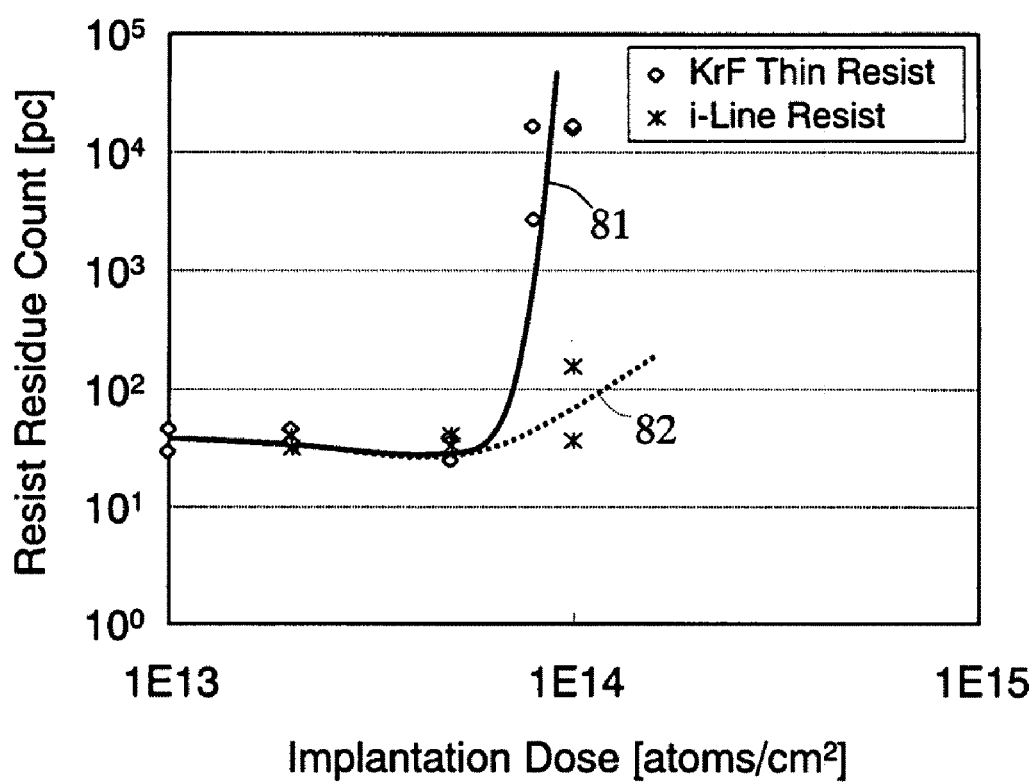
FIG. 10 is a graphical representation showing the relationship between the implantation dose and the resist residue count.

FIG. 10 is a graphical representation showing the dependency of the fine particle defect count (resist residue count) after removal of the photoresist film 3 following ion implantation on the implantation dose in the evaluation substrates having the i-line resist or KrF thin resist in FIG. 9. In FIG. 10, diamond and solid line data 81 represent the KrF thin resist and asterisk and dotted line data 82 represent the i-line resist. Here, the implantation ions are phosphorus ions ($P^+$). The photoresist film 3 is removed by rinsing with ammonium hydroxide-hydrogen peroxide mixture (APM) at 60° C. for 5 minutes and rinsing with sulfuric acid-hydrogen peroxide mixture (SPM) at approximately 140° C. for 7 minutes. In FIG. 10, the horizontal axis corresponds to the implantation dose and the vertical axis corresponds to the resist residue count.

It is understood from FIG. 10 that the different photoresist films 3 exhibit different resist removal properties to the rinsing agents. The KrF thin resist has a significant increase in the resist residue count around an implantation dose of $1 \times 10^{14}/cm^2$ compared to the i-line resist. The resist residue count obtained here results from the degenerated layer 12 produced by the ion implantation. The results in FIG. 10 suggest that the KrF thin resist is subject to a larger degree of hardening or degeneration than the i-line resist.

The relationship between the difference in surface potential and the implantation dose based on the data as shown in FIG. 9 and the relationship between the implantation dose and the resist residue count as shown in FIG. 10 can previously be obtained for each resist material so that the removal property of a specific photoresist film can be predicted based on the difference in surface potential. In other words, it can be predicted based on the difference in surface potential how much resist residue occurs in a specific removal method (the APM and SPM rinsing in FIG. 10) after a specific photoresist film is subject to ion implantation at a specific implantation dose.

Figure 11:
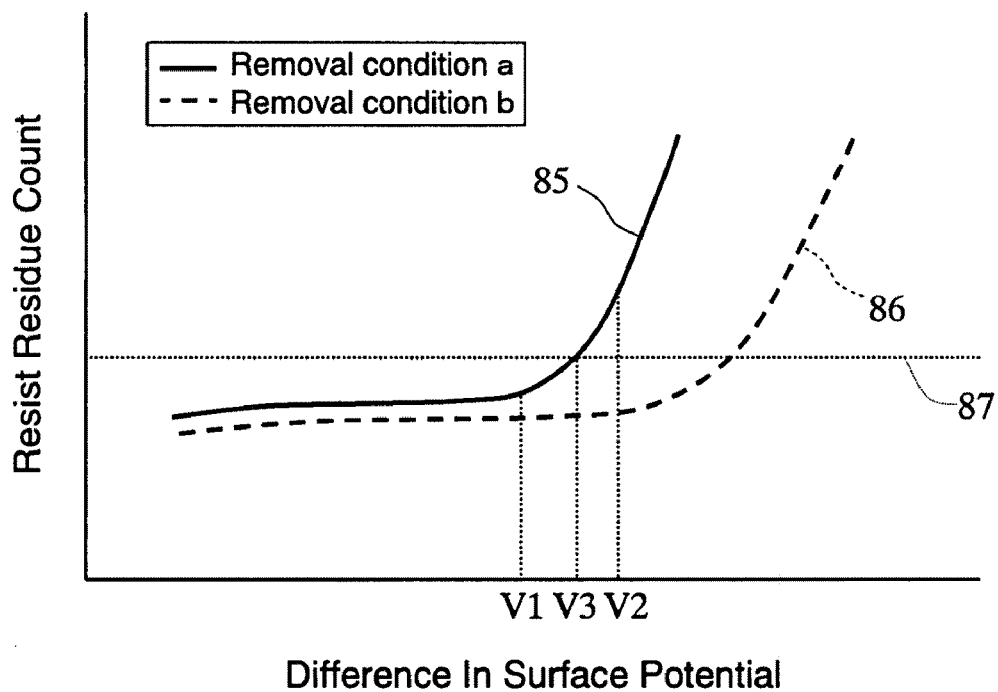
FIG. 11 is a graphical representation showing the relationship between the difference in surface potential and the resist residue count.

FIG. 11 is a graphical representation showing the relationship between difference in surface potential and the resist residue count when the specific removal methods are applied to the photoresist film on which ions are implanted. Data in FIG. 11 are obtained by using respective photoresist films to which the same kind of ions are implanted at the different implantation dose (at the same dose rate) which is relatively low and not exceeding the critical potential. In FIG. 11, data 85 indicated by solid line data 85 show a relationship between difference in surface potential and resist residue count when a standard removal condition (removal condition a) used for in the manufacturing process of an object to be evaluated. Data 86 indicated by broken line data 86 show a relationship between difference in surface potential and resist residue count when a removal condition with strengthened removability (removal condition b) in which such as temperature and time for processing are changed from the standard removal condition. A threshold value 87 indicated by dotted line in FIG. 11 show a maximum value of particle count allowable in the manufacturing process of an object to be evaluated.

As shown in FIG. 11, the resist residue count increases as the difference in the surface potential increases. For example, referring to data 85, when the difference in surface potential is V1, the resist residue count less than or equal to the allowable maximum value is realized. When the difference in surface potential is V2, however, it is predicted that the resist residue count is beyond the allowable maximum value. In such a case, when the difference in surface potential is less than or equal to V3 corresponding to the resist residue count matched to the allowable resist residue count, the resist residue count less than or equal to the allowable maximum value is realized. Further, even when the difference in surface potential is V2, the resist residue count less than or equal to the allowable resist residue count is realized by changing the removal condition to the condition with strengthened resist removability (data 86). Namely, measuring the difference in surface potential allows to determine the extent of the resist residue count, and in parallel to select the removal condition which is optimum for the resist residue count to be less than or equal to the allowable maximum value and which minimizes damages to the semiconductor device during manufacturing. Although the example shown in FIG. 11 illustrates the resist residue count-difference in surface potential curve in the range at relatively low dose, even in ranges at medium dose and high dose the resist residue count-difference in surface potential curve corresponding to the respective dose range and resist removal condition is prepared. Then, based on the prepared curve and the result of the difference in surface potential measurement, the resist residue count is predicted and the optimum removal condition to be within the allowable resist residue counts in the manufacturing process of the semiconductor device is determined.

As described above, a reference range of differences in surface potential (evaluation criteria) is determined in advance according to an allowable range of resist residue counts (the physical quantity varying in response to an achievement of a given treatment) in the manufacturing process of a semiconductor integrated circuit device. Depending on whether or not the measured difference in surface potential is within the reference range of differences in surface potential, it can be determined whether or not the process conditions such as the ion implantation dose, resist removal method, and resist removal conditions are adequate. The evaluation can also be made by determining whether or not the resist residue count predicted from the difference in surface potential is within the allowable range based on the relationship between the difference in surface potential and the implantation dose and the relationship between the implantation dose and the resist residue count.

FIGS. 9 and 10 described above show the relationships with regard to the ion implantation. However, a similar evaluation can be made for dry etching. In such a case, the ion species is replaced with the etching gas species and the implantation dose is replaced with high frequency power for generating plasma or etching time in the etching. The physical quantity that is an indicator of the removal property can be the resist residue count as in FIG. 10.

As described above, the present invention easily evaluates a resin film for formation of a degenerated layer by obtaining the difference in surface potential without actually removing the resin film and obtaining the residue count.

Because of the above described mechanism of formation of a degenerated layer, the difference in surface potential corresponds to the electric resistance that is an indicator of the degree of carbon cross-linkage or carbonization in the carbon-containing polymer structure constituting the resin film as long as the sample (evaluation substrate) has the same structure. The resin film material is an insulating material. Therefore, different resin film materials have more or less the same electric resistance if they are subject to more or less the same degree of carbon cross-linkage or carbonization. In other words, different film materials presumably have more or less the same degree of degeneration in the surface layer if they have more or less the same difference in surface potential. Therefore, for example, even when constituents of the photoresist are changed due to changes in such as a baking condition of the photoresist, the degree of degeneration in the degeneration layer and the resist residue count after removal process can be understood by evaluating surface potential. This also allows the present invention to easily evaluate a resin film.

When the degree of degeneration in a resin film caused by irradiation with charged energetic particles such as implantation ions and etching gas plasma is evaluated, it is desirable that the evaluation is available for high irradiation dose of charged energetic particles. To this end, the insulating film formed on the sample substrate (such as the evaluation substrate shown in FIG. 1D) has a sufficient thickness so that the surface potential is not reduced because of leakage after reaching the critical potential in FIG. 4. This is because the difference in surface potential between the insulating film area (silicon oxide film area) and the resin film area (photoresist film area) in the presence of leakage through the insulation film is determined according to a different mechanism from the mechanism for the difference in potential between the two areas in the absence of leakage through the insulating film.

When a resin film is evaluated in the case of ion implantation, the insulating film at least has to have a thickness of $Rp1+3\Delta Rp1$ or larger ($Rp1$ is the projected range of the implantation ions in the insulating film and $\Delta Rp1$ is the standard deviation of the projected range $Rp1$). The resin film at least has to have a thickness of $Rp2+3\Delta Rp2$ or larger ($Rp2$ is the projected range of the implantation ions in the resin film and $\Delta Rp2$ is the standard deviation of the projected range $Rp2$). The substrate on which the insulating and resin films are deposited can entirely be made of an insulating material.

(Second Evaluation Method Using Surface Potential Measurement)

The surface potential measurement of the present invention can be used to evaluate the immunity against an electrical charging due to irradiation with charged energetic particles as described below in addition to the evaluation with regard to the degenerated layer in the resin layer as described above. This evaluation is effective for thin insulating films or silicon oxide films having a thickness of 100 nm or smaller on the evaluation substrate in FIG. 5.

In such a case, first, an ion species such as phosphorus is implanted in the evaluation substrates with a photoresist film having a fixed area of an opening at several different implantation doses, for example, in a range from $1 \times 10^{11}/cm^2$ to $5 \times 10^{14}/cm^2$, respectively. Then, the surface potential of the silicon oxide film area is measured for each implantation condition to obtain the relationship between the surface potential and the implantation dose (charged energetic particles irradiation dose).

As described above, the charge 9 charged up in the photoresist film area flows in the silicon oxide film area as soon as the surface layer of the photoresist film 3 starts to degenerate as the implantation dose is increased. Consequently, as shown in FIG. 4, the surface potential on the silicon oxide film 2 is raised. When the surface potential on the silicon oxide film 2 is raised to a certain extent, the surface potential on the silicon oxide film 2 is lowered. This phenomenon that the surface potential of the silicon oxide film area has the largest (maximum) value in the course of changes in implantation dose is observed in the surface potential measurements for the above described evaluation substrates. Therefore, the critical potential or nearly the maximum surface potential immediately before the surface potential on the silicon oxide film 2 is lowered even if the implantation dose is increased, and implantation dose corresponding thereto can be obtained based the relationship between the surface potential of the silicon oxide film area and the implantation dose.

The above implantation dose is the implantation dose at which current leakage occurs through the silicon oxide film 2 when the silicon oxide film 2 and photoresist film 3 are formed on the silicon substrate 1. Consequently, it can be determined whether or not there is a risk of dielectric breakdown or damage in the silicon oxide film or underlying silicon substrate at the pattern edges of the photoresist film 3 during the ion implantation.

Recently, ion implantation and etching using photoresist films having low resist opening rates are increasingly utilized for manufacturing various devices such as CCD image sensors and superfine system ISIs. In the ion implantation for medium current regions (implantation dose of approximately $1 \times 10^{10}$ to $1 \times 10^{14}/cm^2$) using a photoresist film having a low resist opening rate as a mask, amount of accumulated charge per unit volume in degenerated layer 12 is large so that leakage of the charge 9 to the substrate occurs at a thin part of the silicon oxide film when a shallow degenerated layer 12 is formed on the surface of the photoresist film. Research by the inventors of the present invention has revealed that the charging phenomenon due to charged energetic particles irradiation often causes defects such as electrostatic breakdown as a result of gathering charge flowing into the substrate in area where a position is the thickness of the silicon oxide film is significantly changed, for example LOCOS (Local Oxidation of Silicon) edge and the like, in the resist opening. The prior art resin film evaluation using SEM images almost fails to determine influence on the device properties such as charging phenomenon.

However, for given device structure and ion implantation conditions, this evaluation method of the present invention can determine whether or not various resist materials on the evaluation substrate simulating the device structure reach the critical potential under the ion implantation conditions. Consequently, resist films that can prevent problems such as electrostatic breakdown of an insulating film such as a silicon oxide film under a resist film caused by charging phenomenon during the implantation from occurring can easily be selected.

This evaluation method is applicable to the dry etching. In such a case, the high frequency power for generating plasma or etching time in the etching can be used as charged energetic particles irradiation dose instead of the implantation dose.

(Third Evaluation Method Using Surface Potential Measurement)

In the first evaluation method, the degree of degeneration of a resin film caused by irradiation with charged energetic particles is evaluated using an evaluation substrate on which an insulating film having such a thickness that the surface potential of the insulating film does not reach the critical potential is deposited. As shown in FIG. 4, 8A or 8B, when the insulating film (silicon oxide film) does not have such a thickness that it does not reach the critical potential for the charged energetic particles irradiation dose, or when the implantation dose is high in the case of ion implantation, the surface potential on the insulating film reaches the critical potential and then drops. In such a case, as described above, it is difficult to precisely evaluate the resin film based on the surface potential.

The dependency of the surface potential on the resist opening rate (the resin film opening rate) as shown in FIGS. 8A and 8B can be used to determine whether or not the surface potential of the insulating film has reached the critical potential. More specifically, first, multiple evaluation substrates having different resin opening rates are used to measure the surface potential on the insulating film exposed in the opening under a desired charged energetic particles irradiation condition to be evaluated (ion implantation condition and dry etching condition). Then, the relationship between the surface potential on the insulating film and the resin film opening rate as shown in FIGS. 8A and 8B is obtained. Based on this relationship, the minimum resin film opening rate is determined among the evaluation substrates having the resin film opening rates that do not lead to the critical potential. Using the evaluation substrate determined as described above, the degree of degeneration in the photoresist film under the charged energetic particles irradiation condition is evaluated. More specifically, the relationship between the difference in surface potential between the resin film and the insulating film and the physical quantity (such as the resin film residue count) which varies in response to the achievement of the resin film removal process (such as APM and APM rinsing) of the evaluation substrate is obtained (FIGS. 9 and 10). Based on the relationship, a reference range of differences in surface potential corresponding to the allowable resin film residue counts in the manufacturing process of a semiconductor integrated circuit device is determined.

The resin film opening rate determined as described above is the minimum resin film opening rate not leading to the critical potential. Therefore, the resin film can be evaluated in a sensitive and accurate manner by measuring the surface potential of the evaluation substrate having such a resin film opening rate and determining whether or not the difference in surface potential is within the reference range of differences in surface potential.

In the first, second and third evaluation methods using the surface potential as described above, measurements of the surface potentials, changes in the surface potentials, or differences in the surface potentials are simply compared with each other in order to relatively compare the progresses of the formation of a degenerative layer between different resin film materials, between different conditions for forming a resin film of a specific material, between different ion implantation conditions (such as ion species, implantation energy, implantation dose, and dose rate), between different dry etching conditions (such as etching gas species and plasma exciting power). Particularly, the implantation dose is desirably within a range from $1 \times 10^{10}/cm^2$ to $1 \times 10^{14}/cm^2$ and more desirably in a range from $1 \times 10^{12}/cm^2$ to $1 \times 10^{13}/cm^2$ in evaluation with regard to the ion implantation process.

(Surface Potential Measuring System)

Figure 12:
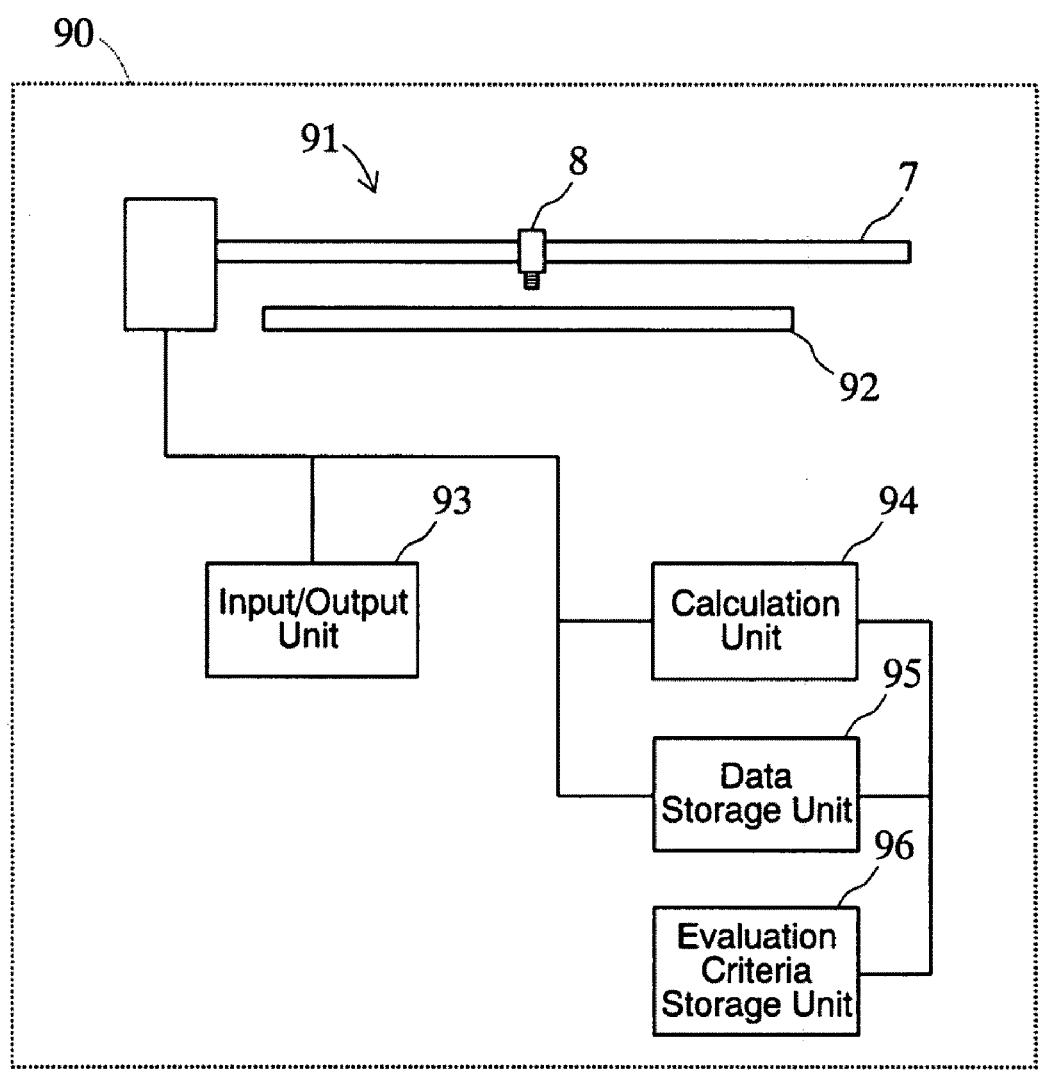
FIG. 12 is a schematic diagram showing the structure of the surface potential measuring system according to an embodiment of the present invention.

FIG. 12 is a schematic diagram showing a surface potential measuring system 90 of the present invention that can be used for implementing the above described the first, second and third evaluation methods. The system comprises a surface potential measuring apparatus 91 having the sensor 8 and guide 7 shown in FIG. 1D and a stage 92 on which the evaluation substrate shown in FIG. 1D and some other figures is placed.

The surface potential measuring system 90 is simply required to have a mechanism that allows the sensor 8 to move over the evaluation substrate from one end to the other thereof via above the opening 4 as explained in FIG. 1D. The stage 92 can be rotated by a specific angle step so that the sensor 8 can move over the evaluation substrate from one end to the other thereof to measure the surface potentials at each angle step. In such a case, not only a surface potential distribution on the evaluation substrate in a diameter direction but also a two-dimensional surface potential distribution on the evaluation substrate can be obtained.

As shown in FIG. 12, the surface potential measuring system 90 comprises an input/output unit 93, a calculation unit 94, a data storage unit 95, and an evaluation criteria storage unit 96. The input/output unit 93 receives experimental condition data such as ion implantation energy and implantation dose for ion implantation directly or in a data format recognizable by the surface potential measuring system 90. The input/output unit 93 outputs measurement data such as surface potentials and evaluation results such as determination results. The calculation unit 94 performs various calculations and evaluating determinations based on surface potential measurement data and controls the surface potential measuring apparatus 91 and various data transfers. The calculation unit 94 can be realized for example by a dedicated arithmetic circuit or hardware having a processor and a memory such as RAM and ROM and software stored in the memory and running on the processor.

The data storage unit 95 and evaluation criteria storage unit 96 consist of a storage devise such as a HDD (hard disk drive). The data storage unit 95 stores surface potential measurement data and various calculation results from the calculation unit 94. The evaluation criteria storage unit 96 stores critical potentials necessary for the calculation unit 94 to determine the measurement results, data regarding the dependency of resist residue count on difference in surface potential for various resist films, and reference ranges of differences in surface potential corresponding to allowable resist residue counts.

The surface potential measuring system 90 of the present invention operates as follows for implementing the above described the first evaluation method. First, an evaluation substrate irradiated with charged energetic particles is placed on the state 92. The evaluation substrate has a silicon substrate 1 on which an insulating film such as a silicon oxide film 2 and a resin film such as a resist film with an opening having a given opening rate are formed in this order from the bottom as shown in FIG. 1B. Then, irradiation doses and energy of charged energetic particles irradiated to the substrate and data regarding the substrate structure (the thicknesses and materials of the insulating and resin films) are supplied from the input/output unit 93.

When the surface potential measuring apparatus 91 receives a surface potential measuring start instruction via the input/output unit 93, the surface potential measuring apparatus 91 measures surface potentials of the region at least from the resin film to the insulating film exposed in the opening of the resin film on the evaluation substrate placed on the stage 92. The measurement results are stored in the data storage unit 95. Then, the calculation unit 94 calculates the difference in surface potential between the resin film and the insulating film based on the surface potential measurement data stored in the data storage unit 95. The calculation unit 94 further compares the reference difference in surface potential stored in the evaluation criteria storage unit 96 with the calculated difference in surface potential and determines whether or not the resin film is appropriate for the manufacturing process according to the above described procedure.

The determination result is displayed on a display screen of the input/output unit 93 or output as electronic data in a given format via the input/output unit 93.

The operation is described above for the first evaluation method. The components of the system operate as required for implementing the other evaluation methods.

(Method for Manufacturing a Semiconductor Device)

A method for manufacturing a semiconductor device applying the evaluation method for the insulating film as described above will be explained in the following. FIG. 13 is a series of cross-sectional views showing an example process of the method for manufacturing a semiconductor device in accordance with the present invention. Here, the present invention is specified by an embodiment of manufacturing the semiconductor device provided with a p-channel transistor and an n-channel transistor. The n-channel transistor is illustrated on the right side, and the p-channel transistor is illustrated on the left side in FIG. 13.

Figure 13A:
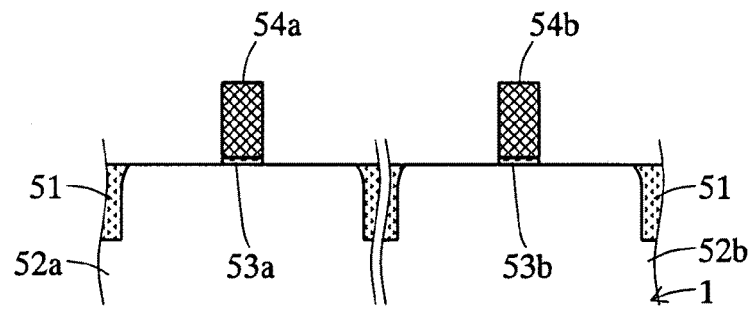
FIGS. 13A to 13D are a series of cross-sectional views showing a manufacturing process for a semiconductor device according to an embodiment of the present invention.

As shown in FIG. 13A, the p-channel transistor and the n-channel transistor are formed on a surface region of a semiconductor substrate 1 separated by an element isolation insulating film 51. The p-channel transistor is provided with a gate electrode 54*a* formed on an n-type well layer 52*a* with a gate insulating film 53*a* therebetween. The n-channel transistor is provided with a gate electrode 54*b* formed on a p-type well layer 52*b* with a gate insulating film 53*b* therebetween.

Figure 13B:
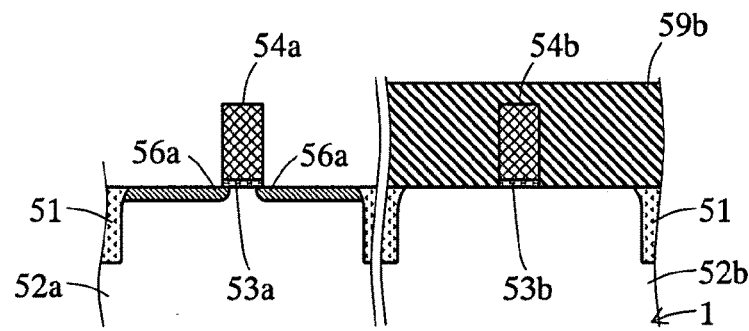
Figure 13C:
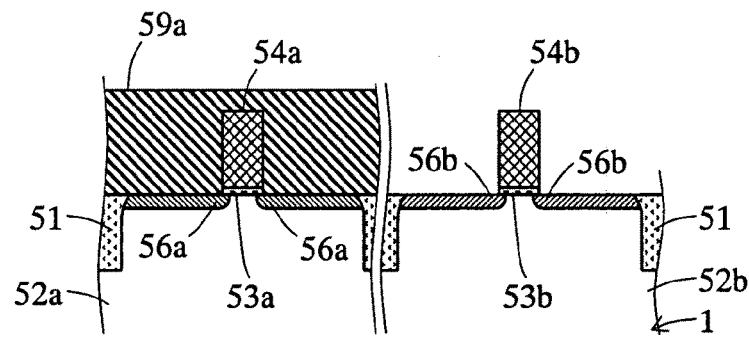

When an extension region in the p-channel transistor is formed, as shown in FIG. 13B, a resist pattern 59*b* which covers a formation region of the n-channel transistor is formed using photolithography technique. In this state, p-type impurity ions are implanted at the implantation dose of $1 \times 10^{10}/cm^2$ to $3 \times 10^{14}/cm^2$, and p-type extension regions 56*a* are formed on both sides of the gate electrodes 54*a* on the surface of the semiconductor substrate 1. Concurrently, a degenerated layer is formed in a surface portion of a resist pattern 59*b*. In the course of this process, ion implantation with same condition as described above is performed on a substrate for measuring surface potential (evaluation substrate). The substrate for measuring surface potential has an insulating layer (a silicon oxide film) with a given thickness on the silicon substrate 1 and a resist pattern composed of the same material as the resist pattern 59*b* formed on the insulating layer as shown in FIG. 1.

Subsequently, a surface potential distribution on the ion-implanted substrate for measuring surface potential is measured by the surface potential measuring system 90. Based on the obtained surface potential distribution, a difference in surface potential between the resist pattern and the region where the resist pattern is not formed on the substrate for measuring surface potential is calculated.

Based on a predetermined relationship between the difference in surface potential and resist residue count, the calculation unit 94 in the surface potential measuring system 90 determines whether or not the resist pattern 59*b* is removable by the removal condition employed in the manufacturing process of the semiconductor device. The removal condition is not particularly limited, however, in the manufacturing process of the semiconductor device, only chemical solution is used without using the oxygen plasma treatment to remove the resist pattern 59*b*. Generally, the standard removal condition is to rinse with APM at 60° C. for 5 minutes and then rinse with SPM at approximately 140° C. for 7 minutes. Thus, it is prevented that the silicon oxide film on the p-type extension region 56*a* which increases sheet resistance in the p-type extension region 56*a* is formed. In addition, it is prevented that the silicon oxide film which hampers ion from entering the semiconductor substrate 1 is formed when ion implantation in order to form an n-type extension regions on the both sides of the gate electrode 54*b* on the surface of the semiconductor substrate of the n-channel transistor formation area.

In this example, the calculation unit 94 determines as removable when the calculated difference in surface potential is less than or equal to a maximum value of the allowable difference in surface potential or the calculated difference in surface potential is within a allowable range. Also, the calculation unit 94 determines as non-removable under the removal condition when the calculated difference in surface potential is more than the maximum value or the calculated difference in surface potential is outside of the allowable range. The maximum value and the allowable range is determined by obtaining the difference in surface potential according to an allowable resist residue count in the manufacturing process of the semiconductor device based on the relationship between the difference in surface potential and the resist residue count as shown in FIG. 11.

When determined as removable, the resist pattern 59*b* is removed under the resist removal condition. When determined as non-removable, as understood with reference to FIG. 11, the resist pattern 59*b* is removed by changing the resist removal condition so that the resist residue count becomes within the allowable range even with the measured difference in surface potential. The removal process is performed under the condition of which at least either of chemical solution temperature or removal time in APM rinsing and SPM rinsing is increased, for example.

The resist pattern 59*b* is removed based on the determination results, and in succession, the extension region of the n-type transistor is formed. When forming the extension region of the n-type transistor, the resist pattern 59*a* to cover a formation region of the p-channel transistor is formed using a photolithography technique. In this state, n-type impurity ions are implanted at the implantation dose of approximately $1 \times 10^{10}/cm^2$ to $3 \times 10^{14}/cm^2$, and n-type extension regions 56*b* are formed on both sides of the gate electrodes 54*b* on the surface of the semiconductor substrate 1. Concurrently, a degenerated layer is formed in a surface portion of a resist pattern 59*a*. In the course of this process as well, ion implantation with same condition is performed on a substrate for measuring surface potential on which a resist pattern composed of the same material as the resist pattern 59*a* on an insulating layer.

Subsequently, a surface potential distribution on the substrate for measuring surface potential is measured using the surface potential measuring system 90, and based on the obtained surface potential distribution, a difference in surface potential between the resist pattern and the region where the resist pattern is not formed on the substrate for measuring surface potential is calculated. Then, it is determined whether or not the resist pattern 59*a* is removable based on the conditions employed in the manufacturing process of the semiconductor device by using a method applied for forming the extension region in the p-channel transistor. When determined as removable, the resist pattern 59*a* is removed under the resist removal condition. When determined as non-removable, the resist pattern 59a is removed by changing the resist removal condition as the same method as used for forming the extension region of the p-channel transistor.

Figure 13D:
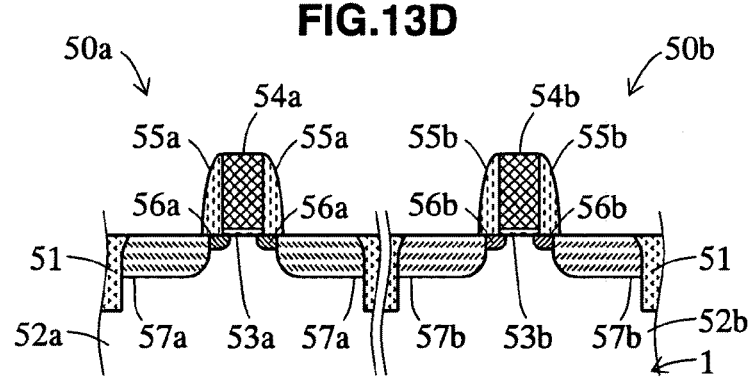
Figure 14A:
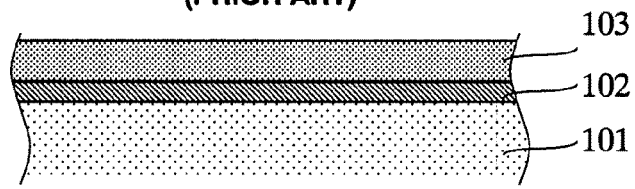
FIGS. 14A to 14E are cross-sectional views showing the steps of the prior art resin film evaluation method.
Figure 14B:
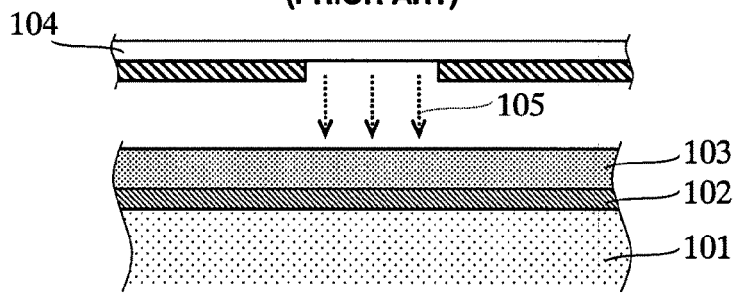
Figure 14C:
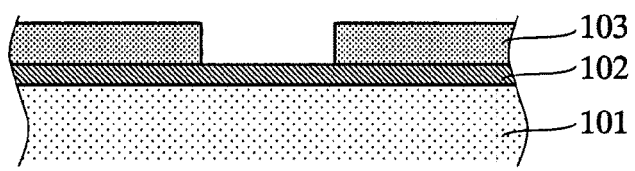
Figure 14D:
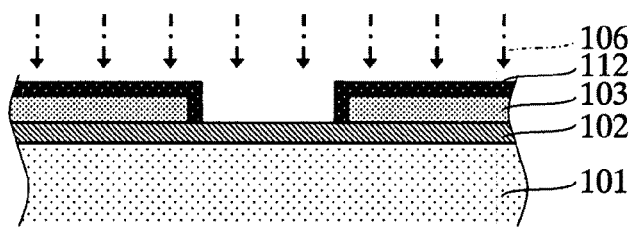
Figure 14E:
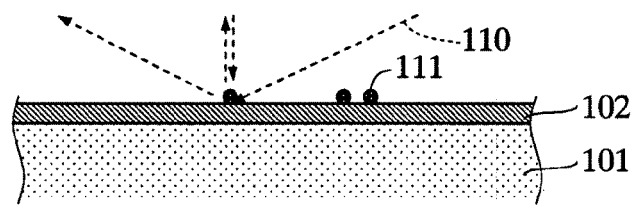
Figure 15A:
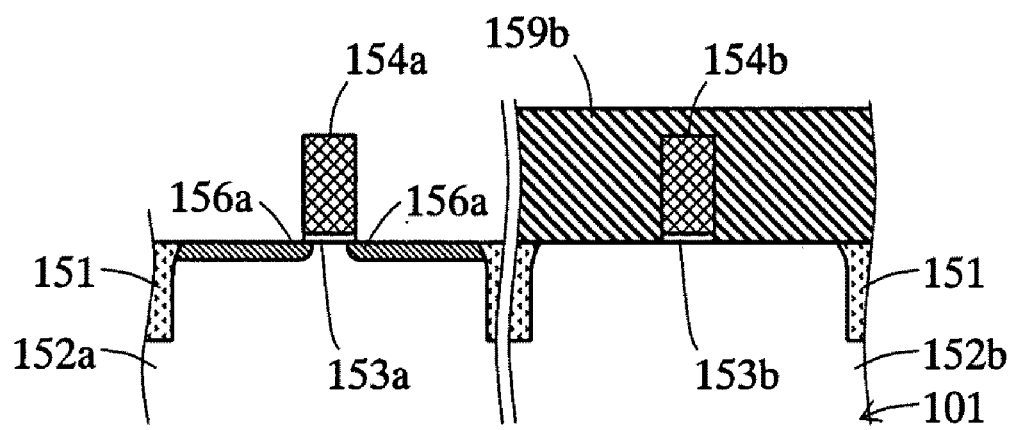
FIGS. 15A and 15B are cross-sectional views showing the inconvenience caused by using oxygen plasma treatment.
Figure 15B:
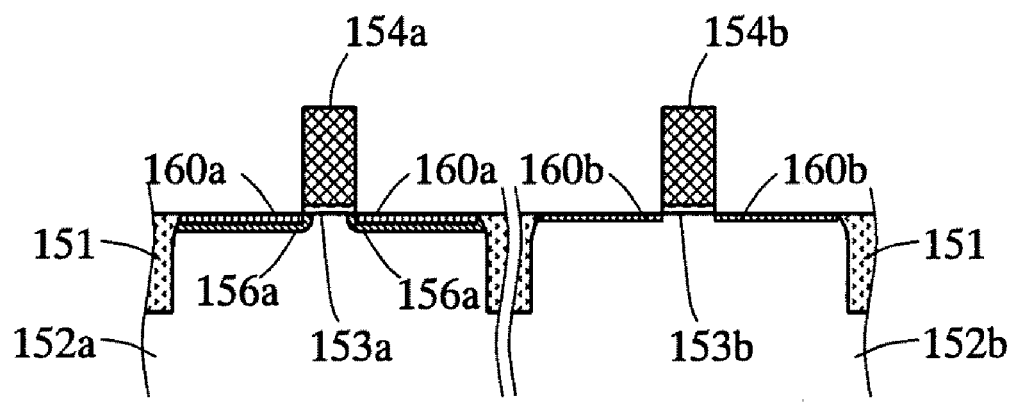

After the resist pattern 59a is removed based on the determination result, sidewalls 55a are formed on both sides of the gate electrodes 54a, and concurrently sidewalls 55b are formed on both sides of the gate electrodes 54b. P-type impurity ions are implanted to the semiconductor substrate 1 in a state that the resist pattern (not shown) to cover the n-channel transistor formation region is formed on the semiconductor substrate 1, and thereby p-type high concentration impurity regions 57a having a function as a source region or a drain region of the p-channel transistor are formed. In the meantime, n-type impurity ions are implanted to the semiconductor substrate 1 in a state that the resist pattern (not shown) to cover the p-channel transistor formation region is formed on the semiconductor substrate 1, and thereby n-type high concentration impurity regions 57b having a function as a source region or a drain region of the p-channel transistor are formed. In this way, as shown in FIG. 13D, a p-channel transistor 50a and an n-channel transistor 50b are formed on the semiconductor substrate 1.

According to the method for manufacturing a semiconductor device of the present invention, it can be easily determined in short time where or not the resist pattern can be removed under the predetermined removal condition. Therefore, production throughput can be enhanced as compare with the manufacturing process of detecting particle abnormality by counting number of particles (resist residue count) on the semiconductor substrate. Further, the resist pattern is reliably removed without generating particles by changing the resist removal condition to an optimum condition based on the measured difference in surface potential.

The example in which the above described determination is applied to ion implantation to form the extension regions in the p-channel transistor and the n-channel transistor formed on the same substrate, however, that is appropriate for a process in which ion is implanted with the implantation dose of approximately $1 \times 10^{10}/cm^2$ to $1 \times 10^{14}/cm^2$. Therefore, the above described determination is applicable to the removal of the resist pattern used for an ion implantation process in order to form an impurity region which is a reverse conductivity type with an extension region and has higher impurity concentration than a well layer (so-called pocket region) in a state covering the periphery of the extension region as not shown in FIGS. 13A to 13D. Also, he above described determination is applicable to the removal of the resist pattern used for an ion implantation to introduce impurity ion into the channel region in order to adjust threshold voltage. Further, besides the transistors, it is applicable to the removal of the resist pattern used for an ion implantation process to introduce impurity ion in order to reduce a surface leak current on a surface of a photodiode provided by such as a solid-state imaging devices.

As described above, the present invention provides a simple and highly accurate method of evaluating the state of a degenerated layer formed on the surface of a resin film such as a photoresist due to charged energetic particles such as implantation ions, for which there is no effective means in the prior art. The present invention is significantly effective in evaluating the adequacy of a resin film in the manufacturing process of a semiconductor integrated circuit device.

The present invention is not restricted to the above described embodiments. Various modifications and applications can be available within the effective range of the present invention. For example, the above explanation is made mainly for the photoresist resin film and silicon oxide insulating film. However, the resin film and insulating film can be of any materials. In the above explanation, the physical quantity varying in response to the achievement of the resin film removal process is the resist residue count (resin film residue count). The physical quantity can be a resist residue density (the resin film residue count per unit area). When a treatment other than the resin film removal is performed after the charged energetic particles irradiation, the physical quantity can be any physical quantity that gives a quantitative measurement for the result of the treatment.

The present invention can easily determine the adequacy of a resin film such as a photoresist film in the manufacturing process, providing an effective resin film evaluation method in selecting a most suitable resist for implantation or etching and method for manufacturing a semiconductor device.

The invention claimed is:

1. A resin film evaluation method, comprising the steps of:
   irradiating with charged energetic particles a substrate having a resin film formed on an insulating layer with an opening in which the surface of the insulating layer is exposed;
   measuring surface potentials of the substrate surface irradiated with the charged energetic particles;
   obtaining the difference in surface potential between the resin film and the insulating film exposed in the opening; and
   estimating a physical quantity varying in response to a achievement of a treatment performed on the resin film irradiated with the charged energetic particles based on the difference in surface potential.

2. A resin film evaluation method according to claim 1, further comprising a step of determining whether or not the estimated physical quantity is within a predetermined allowable range or whether or not the difference in surface potential is within a range of differences in potential corresponding to the allowable range, thereby determining whether or not the material of the resin film, irradiation conditions of the charged energetic particles, or treatment conditions for the resin film are appropriate.

3. A resin film evaluation method, comprising the steps of:
   irradiating multiple substrates each having a resin film formed on an insulating layer of a given thickness with a fixed area of an opening in which the surface of the insulating layer is exposed with charged energetic particles at different irradiation doses, respectively; measuring surface potentials of the insulating films exposed in the opening of the each substrate irradiated with the charged energetic particles and obtaining the relationship between the surface potential and the charged energetic particles irradiation dose; obtaining a charged energetic particles irradiation dose leading to the critical potential which is the maximum surface potential of the insulating film exposed in the opening based on the relationship; and determining whether or not charge accumulated in the insulating film due to the charged energetic particles flows through the insulating film at a given charged energetic particles irradiation dose based on the critical potential or the charged energetic particles irradiation dose corresponding to the critical potential.

4. A resin film evaluation method, comprising the steps of:
   irradiating multiple substrates each having one of multiple resin films of different constituents formed on an insulating layer with an opening in which the surface of the insulating layer is exposed with charged energetic particles under a given condition;
   measuring surface potentials of the multiple substrates irradiated with the charged energetic particles;

obtaining the difference in surface potential between the resin film and the insulating film exposed in the opening on the each substrate; and comparing the differences in surface potential, thereby comparing the progresses of degeneration of degenerated layers that occur in the each resin film when the each substrate is irradiated with the charged energetic particles.

5. A resin film evaluation method according to claim 1, wherein the difference in surface potential is the difference in surface potential between the resin film and the insulating film in the area including an edge of the opening.

6. A resin film evaluation method according to claim 4, wherein the difference in surface potential is the difference in surface potential between the resin film and the insulating film in the area including an edge of the opening.

7. A resin film evaluation method according to claim 1, wherein the treatment performed on the resin film is a removal process of the resin film and the physical quantity is a residue count or residue density of the resin film after the resin film removal process.

8. A resin film evaluation method according to claim 7, wherein the resin film removal process is a chemical solution removal process.

9. A resin film evaluation method according to claim 1, wherein the charged energetic particles are implantation ions and the resin film is a photoresist.

10. A resin film evaluation method according to claim 3, wherein the charged energetic particles are implantation ions and the resin film is a photoresist.

11. A resin film evaluation method according to claim 4, wherein the charged energetic particles are implantation ions and the resin film is a photoresist.

12. A resin film evaluation method according to claim 1, wherein the charged energetic particles are particles in plasma and the resin film is a photoresist.

13. A resin film evaluation method according to claim 3, wherein the charged energetic particles are particles in plasma and the resin film is a photoresist.

14. A resin film evaluation method according to claim 4, wherein the charged energetic particles are particles in plasma and the resin film is a photoresist.

15. A resin film evaluation method according to claim 9, wherein the insulating film at least has a thickness of $Rp1+3\Delta Rp1$ or larger where $Rp1$ is a projected range of the implanted ions in the insulating film and $\Delta Rp1$ is a standard deviation of the projected range.

16. A resin film evaluation method according to claim 10, wherein the insulating film at least has a thickness of $Rp1+3\Delta Rp1$ or larger where $Rp1$ is a projected range of the implanted ions in the insulating film and $\Delta Rp1$ is a standard deviation of the projected range.

17. A resin film evaluation method according to claim 11, wherein the insulating film at least has a thickness of $Rp1+3\Delta Rp1$ or larger where $Rp1$ is a projected range of the implanted ions in the insulating film and $\Delta Rp1$ is a standard deviation of the projected range.

18. A resin film evaluation method according to claim 9, wherein the photoresist at least has a thickness of $Rp2+3\Delta Rp2$ or larger where $Rp2$ is a projected range of the implanted ions in the photoresist and $\Delta Rp2$ is a standard deviation of the projected range.

19. A resin film evaluation method according to claim 10, wherein the photoresist at least has a thickness of $Rp2+3\Delta Rp2$ or larger where $Rp2$ is a projected range of the implanted ions in the photoresist and $\Delta Rp2$ is a standard deviation of the projected range.

20. A resin film evaluation method according to claim 11, wherein the photoresist at least has a thickness of $Rp2+3\Delta Rp2$ or larger where $Rp2$ is a projected range of the implanted ions in the photoresist and $\Delta Rp2$ is a standard deviation of the projected range.

21. A resin film evaluation method according to claim 4, wherein the charged energetic particles are implantation ions, the resin film is a photoresist, and the implantation dose of ion implantation is $1\times10^{10}/cm^2$ to $1\times10^{14}/cm^2$.

22. A method for manufacturing a semiconductor device having an impurity region formed by ion implantation, comprising the steps of:

forming a first resist pattern on a semiconductor substrate;

forming an impurity region in the semiconductor substrate by ion implantation using the first resist pattern as a mask;

performing ion implantation under the same ion implantation condition of the semiconductor substrate to an evaluation substrate on which a second resist pattern made of the same material as the first resist pattern having an opening in which a insulating film is exposed on the insulating film formed on a substrate;

measuring surface potentials on the second resist pattern and the insulating film on the evaluation substrate;

determining whether or not the first resist pattern is removable under a predetermined condition based on a difference in the measured surface potentials between the second resist pattern and the insulating film; and when determined as non-removable, changing the resist removal condition to which the first resist pattern is removable even with the difference in the measured surface potentials between the second resist pattern and the insulating film, and removing the first resist pattern under the changed condition.

23. A method for manufacturing a semiconductor device according to claim 22, wherein determination whether or not the second resist pattern is removable is performed whether or not a resist residue count or a resist residue density after removal of resist pattern which corresponds the difference in the measured surface potentials between the second resist pattern and the insulating film is within an allowable range in the manufacturing process of the semiconductor device.

24. A method for manufacturing a semiconductor device according to claim 22, wherein an implantation dose of the ion implantation is $1\times10^{10}/cm^2$ to $3\times10^{14}/cm^2$.

25. A method for manufacturing a semiconductor device according to claim 22, wherein the resist pattern is removed by using only chemical solution.

* * * * *